(12) United States Patent
Ding et al.

(10) Patent No.: US 7,705,009 B2
(45) Date of Patent: Apr. 27, 2010

(54) 4-AMINOPYRIMIDINE-5-THIONE DERIVATIVES

(75) Inventors: Qingjie Ding, Bridgewater, NJ (US); Nan Jiang, Fairfield, NJ (US); Allen John Lovey, North Caldwell, NJ (US)

(73) Assignee: Hoffman-La Roche Inc., Nutley, NJ (US)

( * ) Notice: Subject to any disclaimer, the term of this patent is extended or adjusted under 35 U.S.C. 154(b) by 842 days.

(21) Appl. No.: 11/581,529

(22) Filed: Oct. 16, 2006

(65) Prior Publication Data

US 2007/0117821 A1 May 24, 2007

Related U.S. Application Data

(60) Provisional application No. 60/738,915, filed on Nov. 22, 2005.

(51) Int. Cl.
*C07D 239/48* (2006.01)
*C07D 405/14* (2006.01)
*C07D 413/14* (2006.01)
*A61K 31/506* (2006.01)

(52) U.S. Cl. .................. 514/275; 544/323; 544/324; 544/325

(58) Field of Classification Search .............. 544/323, 544/324, 325; 514/275
See application file for complete search history.

(56) References Cited

U.S. PATENT DOCUMENTS

| 5,654,307 | A | 8/1997 | Bridges et al. |
| 6,107,305 | A | 8/2000 | Misra et al. |
| 6,262,096 | B1 | 7/2001 | Kim et al. |
| 6,552,029 | B1 * | 4/2003 | Davis et al. .............. 514/275 |
| 6,569,878 | B1 | 5/2003 | Chong et al. |
| 6,756,374 | B2 | 6/2004 | Chen et al. |
| 6,818,663 | B2 | 11/2004 | Chu et al. |
| 2002/0151554 | A1 | 10/2002 | Chen et al. |
| 2002/0198171 | A1 | 12/2002 | Schinazi et al. |
| 2004/0006058 | A1 | 1/2004 | Chu et al. |
| 2004/0024208 | A1 * | 2/2004 | Das et al. ................ 544/137 |
| 2004/0063737 | A1 | 4/2004 | Lucking et al. |
| 2004/0082595 | A1 | 4/2004 | Ding et al. |
| 2004/0087594 | A1 | 5/2004 | Ding et al. |
| 2004/0102630 | A1 | 5/2004 | Brumby et al. |
| 2004/0162303 | A1 | 8/2004 | Bartkovitz et al. |
| 2005/0239843 | A1 | 10/2005 | Ding et al. |
| 2005/0277655 | A1 | 12/2005 | Ding et al. |
| 2006/0229330 | A1 | 10/2006 | Bartkovitz et al. |

FOREIGN PATENT DOCUMENTS

| JP | 48049776 | 7/1973 |
| WO | WO 91/18887 | 12/1991 |
| WO | WO 00/12485 | 3/2000 |
| WO | WO 00/39101 | 7/2000 |
| WO | WO 01/60816 | 8/2001 |
| WO | WO 01/64653 | 9/2001 |
| WO | WO 01/64654 | 9/2001 |
| WO | WO 01/64656 | 9/2001 |
| WO | WO 01/79198 | 10/2001 |
| WO | WO 2004/014904 | 2/2004 |
| WO | WO 2004/048343 | 6/2004 |
| WO | WO 2004/069139 | * 8/2004 |
| WO | WO 2005/037800 | 4/2005 |

OTHER PUBLICATIONS

Harris, W. and Wilkinson, S., Emerging Drugs . . . 2000, 5, 287-297.
Dumas, J., Exp. Opin. Ther. Patents. 2001, 11, 405-429.
Sielecki T., et. al., J. Med. Chem . . . 2000, 43, 1-18.
Chu, Xin-Jie et al., 2,4-Diamino-5-ketopyrimidines: Synthesis and structure-activity relationships of a series of novel and potent CDK inhibitors. Abstracts of Papers, 230th ACS National Meeting, Washington, DC, United States, Aug. 28-Sep. 1, 2005, MEDI-400. CODEN: 69HFCL AN 2005:739908 CAPLUS.
Moliterni, John et al., Synthesis of 2,4-diamino-5-ketopyrimidines as novel and potent CDK inhibitors: Utilization of a facile metal/halogen exchange initiated by isopropyl magnesium chloride. Abstracts of Papers, 230th ACS National Meeting, Washington, DC, United States, Aug. 28-Sep. 1, 2005, MEDI-398. CODEN: 69HFCL AN 2005:739906 CAPLUS.
Abstracts of Papers, 230th ACS National Meeting, Washington, DC, United States, Aug. 28-Sep. 1, 2005, MEDI-397. CODEN:69HFCL AN 2005:739908 CAPLUS.
Abstracts of Papers, 229th ACS National Meeting, San Diego, CA, United States, Mar. 13-17, 2005, MEDI-138. CODEN: 69GQMP An 2005:191471 CAPLUS.
Bridges, A.J., Exp. Opin. Ther. Patents. 1995, 5, 12451257.
Barvian et al., J. Med. Chem., 2000, 43, 4606-4616.
Chong, W., Fischer, Curr. Opin. in Drug Discov. and Develop., 2001, 4, 623-634.
Hamdouchi et al., Molecular Cancer Therapeutics, 2004, vol. 3(1), pp. 1-9.
Jaramillo, et al., Bioorganic & Medicinal Chemistry Letters, 14, 2004, pp. 6095-6099.

* cited by examiner

*Primary Examiner*—Deepak Rao
(74) *Attorney, Agent, or Firm*—George W. Johnston; Patricia S. Rocha-Tramaloni

(57) ABSTRACT

Novel 4-aminopyrimidine-5-thione derivatives are disclosed. These compounds inhibit cyclin-dependent kinases, in particular Cdk1, Cdk2 and Cdk4. These compounds and their pharmaceutically acceptable salts have antiproliferative activity and are useful in the treatment or control of cancer, in particular solid tumors. This invention is also directed to pharmaceutical compositions containing such compounds and to methods of treating or controlling cancer, most particularly the treatment or control of breast, lung, colon and prostate tumors.

20 Claims, No Drawings

US 7,705,009 B2

4-AMINOPYRIMIDINE-5-THIONE DERIVATIVES

PRIORITY TO RELATED APPLICATIONS

This application claims the benefit of U.S. Provisional Application No. 60/738,915, filed Nov. 22, 2005, which is hereby incorporated by reference in its entirety.

FIELD OF THE INVENTION

The present invention relates to novel 4-aminopyrimidine-5-thione derivatives that inhibit cyclin-dependent kinases. These compounds and their pharmaceutically acceptable salts have antiproliferative activity and are useful, inter alia, in the treatment or control of cancer, in particular solid tumors. This invention also relates to pharmaceutical compositions containing such compounds and to methods of treating or controlling cancer, most particularly the treatment or control of breast, lung, colon and prostate tumors.

BACKGROUND OF THE INVENTION

Uncontrolled cell proliferation is the hallmark of cancer. Cancerous tumor cells typically have some form of damage to the genes that directly or indirectly regulate the cell-division cycle.

The progression of cells through the various phases of the cell cycle is regulated by a series of multienzyme complexes consisting of a regulatory protein, a cyclin, and a kinase. These kinases are called cyclin-dependent kinases (Cdks). The Cdks are expressed throughout the cell cycle, while the levels of the cyclins vary depending on the stage of the cell cycle.

The four primary phases of cell cycle control are generally describes as $G_1$, S, $G_2$, and M. Some essential enzymes for cell cycle control appear to be cyclin D/Cdk4, cyclin D/Cdk6, cyclin E/Cdk2, cyclin A/Cdk2, and cyclin B/Cdk1 (also known as Cdc2/cyclin B). Cyclin D/Cdk4, cyclin D/Cdk6, and cyclin E/Cdk2 control passage through the $G_1$-phase and the $G_1$- to S-phase transition by phosphorylation of the retinoblastoma phosphoprotein, pRb. Cyclin A/Cdk2 regulates passage through the S-phase, and cyclin B/Cdk1 controls the $G_2$ checkpoint and regulates entry into M (mitosis) phase.

The cell cycle progression is regulated by Cdk1 (cdc2) and Cdk2 beyond early $G_1$ when cells are committed to cytokinesis. Therefore, drug inhibition of these Cdks is likely not only to arrest cell proliferation, but also to trigger apoptotic cell death. Once the cells pass the $G_1$ restriction point and are committed to S phase, they become independent of growth factor stimulation for continued cell cycle progression.

Following completion of DNA replication, cells enter the $G_2$ phase of the cell cycle in preparation for M phase and cytokinesis. Cdk1 has been shown to regulate passage of cells through these later phases of the cell cycle in association with both cyclins A and B. Complete activation of Cdk1 requires both cyclin binding and specific phosphorylation (Morgan, D. O., De Bondt, H. L., Curr. Opin. Cell. Biol. 1994, 6, 239-246). Once activated, Cdk1/cyclin complexes prepare the cell for division during M phase.

The transition from $G_1$ phase into S phase as stated above is regulated by the complex of Cdk4 with cyclin D and Cdk2 with cyclin E. These complexes phosphorylate the tumor suppressor protein Retinoblastoma (pRb), releasing the transcription factor E2F and allowing the expression of genes required in S phase (Nevins, J. R. *Science* 1992, 258, 424-429; Lavia, P. *BioEssays* 1999, 21, 221-230). Blocking the activity of the Cdk4/cyclin D and Cdk2/cyclin E complexes arrests the cell cycle in $G_1$ phase. For example, the proteins of the INK4 family, including $p16^{INK4a}$, which block the kinase activity of the Cdk4/cyclin D complex, cause arrest in $G_1$ (Sherr, C. J. *Science* 1996, 274, 1672-1677). The specific block has been reviewed (Vidal, A. *Gene* 2000, 247, 1-15).

Experiments have shown that the complex of Cdk4 with cyclin D3 also plays a role in cell cycle progression through $G_2$ phase. Inhibition of this complex, either by p16 or using a dominant negative Cdk4, results in arrest in $G_2$ phase in cells that do not express pRb (Gabrielli B. G. et al. *J. Biol. Chem.* 1999, 274, 13961-13969).

Numerous defects in the pRb pathway have been shown to be involved in various cancers. For example, over expression of Cdk4 has been observed in cases of hereditary melanoma (Webster, K. R. *Exp. Opin. Invest. Drugs* 1998, 7, 865-887); cyclin D is over expressed in many human cancers (Sherr, C. J. *Science* 1996, 274, 1672-1677); p16 is mutated or deleted in many tumors (Webster, K. R. *Exp. Opin. Invest Drugs* 1998, 7, 865-887); and pRb function is lost through mutation or deletion in many human cancers (Weinberg, R. A. *Cell* 1995, 81, 323-330). Defects in this pathway have also been shown to have an effect on prognosis. For example, loss of p16 is correlated with poor prognosis in non-small-cell lung carcinoma (NSCLC) and malignant melanoma (Tsihlias, J. et al. *Annu. Rev. Med.* 1999, 50, 401-423). Abnormalities of cyclin D1 and/or pRb at the gene and/or expression level were present in more than 90% of a series of non-small cell lung cancer specimens, indicating that cyclin D1 and/or pRb represent an important step in lung tumor genesis (Marchetti, A. et al. *Int. J. Cancer* 1998, 75, 573-582). In 49 out of 50 pancreatic carcinomas (98%), the pRb/p16 pathway was abrogated exclusively through inactivation of the p16 gene and cyclin D connected (Schutte, M. et al. *Cancer Res.* 1998, 57, 3126-3134). For a review on the relation between expression of pRb and the cyclin/cyclin dependent kinases in a number of tissues see Teicher, B. A. *Cancer Chemother. Pharmacol.* 2000, 46, 293-304.

Because of the involvement of the Cdk4/cyclin D/pRb pathway in human cancer through its role in regulating progression of the cell cycle from $G_1$ to S phase, and the potential therapeutic benefit from modulating this pathway, there has been considerable interest in agents that inhibit or promote elements of this pathway. For example, effects on cancer cells have been shown using antibodies, antisense oligonucleotides and over expression or addition of proteins involved in the pathway. See, e.g., Lukas, J. et al. *Nature* 1995, 79, 573-582; Nevins, J. R. *Science* 1992, 258, 424-429; Lim, I. K. et al. *Molecular Carcinogenesis* 1998, 23, 25-35; Tam, S. W. et al. *Oncogene* 1994, 9, 2663-2674; Driscoll, B. et al. *Am. J. Physiol.* 1997, 273 (*Lung Cell. Mol. Physiol.*), L941-L949; and Sang, J. et al. *Chin. Sci. Bull.* 1999, 44, 541-544).

The role of cdks in the regulation of cellular proliferation is thus well established. For example, as shown above, there is an extensive body of literature validating the use of compounds inhibiting targets in the Cdk4, Cdk2 and Cdk1 pathways as anti-proliferative therapeutic agents. Inhibitors of cellular proliferation thus act as reversible cytostatic agents that are useful in the treatment of disease processes which feature abnormal cellular growth, such as cancers and other cell proliferative disorders including, for example inflammation (e.g. benign prostate hyperplasia, familial adenomauosis, polyposis, neurofibromatosis, atherosclerosis, pulmonary fibrosis, arthritis, psoriasis, inflammatory bowel disease, transplantation rejections infections), viral infections (including, but not limited to herpes virus, poxvirus, Epstein-Barr virus), autoimmune disease (e.g. lupus, rheumatoid arthritis, psoriasis, inflammatory bowel disease), neurodegenerative disorders (including but not limited to Alzheimer's disease), and neurodegenerative diseases (e.g. Parkinson's disease, amyotrophic lateral sclerosis, retinitis pigmentosa, spinal muscular atrophy, and cerebral degeneration).

For reviews of compounds inhibiting the Cdk4/cyclin D pathway see, for example: Harris, W. and Wilkinson, S., *Emerging Drugs.* 2000, 5, 287-297; Dumas, J., *Exp. Opin. Ther. Patents.* 2001, 11, 405-429; Sielecki T., et. al., *J. Med. Chem.* 2000, 43, 1-18.

SUMMARY OF THE INVENTION

The present invention relates to novel diaminopyrimidines of the formula

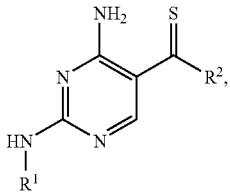

I wherein
$R^1$ is selected from the group
heterocycle and lower alkyl-heterocycle, wherein the heterocycle moiety in both instances optionally may be substituted by up to four substituents independently selected from
H,
lower alkyl,
lower alkyl substituted by oxo, $OR^{12}$, $CO_2R^{12}$, $NR^5R^6$, $S(O)_nR^{15}$ or $C(O)NR^5R^6$,
$CO_2R^7$,
$COR^{11}$,
$COR^{12}$,
$C(O)NR^{13}R^{14}$,
$S(O)_nR^{15}$,
oxo,
$OR^{12}$; or
$NR^5R^6$,
aryl,
aryl substituted by
H,
$S(O)_n$—$R^{15}$,
$NR^5R^6$,
carbonyl,
carbonyl substituted by lower alkyl, $OR^{12}$ or $NR^5R^6$,
lower alkyl,
lower alkyl substituted by $OR^{10}$ or $NR^5R^6$,
$OR^8$;
halogen,
cycloalkyl,
cycloalkyl substituted by $OR^7$, $NR^5R^5$ or $S(O)_nR^{15}$,
lower alkyl, and
lower alkyl substituted by
$NR^5R^6$,
$NR^{11}SO_2R^{15}$,
$CO_2R^{10}$,
$S(O)_nR^{15}$,
heterocycle,
heterocycle substituted by
lower alkyl,
$CO_2R^{12}$ or
$SO_2R^{15}$,
heteroaryl,
heteroaryl substituted by
lower alkyl,
$CO_2R^{12}$, or
$SO_2R^{15}$,
aryl, and
aryl substituted by
lower alkyl,
halogen,
$NR^5R^6$,
$COR^{12}$, or
$CO_2R^{12}$;
$R^2$ is selected from the group
aryl, heteroaryl, cycloalkyl and heterocycle, wherein each may be substituted by up to four substituents independently selected from the group
lower alkyl,
lower alkyl substituted by halogen or $OR^{10}$,
halogen,
$OR^{12}$,
$NO_2$,
CN,
$NR^5R^6$,
$S(O)_n$—$R^9$, and
$SO_2$—$NR^{16}R^{17}$;
$R^5$ and $R^6$ are each independently selected from the group
H,
lower alkyl,
lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo,
cycloalkyl,
cycloalkyl substituted by $CO_2R^{12}$, $OR^{12}$, $NR^{13}R^{14}$, $C(O)NR^{13}R^{14}$ or $SO_2R^{15}$,
aryl,
aryl substituted by $NR^{13}R^{14}$, $OR^{12}$, $CO_2R^{12}$, $C(O)NR^{13}R^{14}$, $SO_2R^{15}$, halogen, lower alkyl, or lower alkyl substituted by halogen, $OR^{12}$, oxo, $CO_2R^{12}$, $C(O)NR^{13}R^{14}$ or $NR^{13}R^{14}$,
$SO_2R^{15}$,
$CO_2R^{12}$, and
$COR^{12}$,
or alternatively, the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $NR^{13}R^{14}$, lower alkyl and lower alkyl substituted by $OR^{12}$;
$R^7$ is selected from the group
H,
lower alkyl,
lower alkyl substituted by $OR^{12}$, $CO_2R^{12}$, $NR^5R^6$, $C(O)NR^5R^6$, halogen and oxo,
cycloalkyl,
cycloalkyl substituted by OH, oxo, or $NH_2$,
$SO_2R^{15}$, and
$COR^{12}$;

$R^8$ is selected from the group
- H,
- lower alkyl,
- lower alkyl substituted by $NR^5R^6$,
- heterocycle, and
- heterocycle substituted by lower alkyl, $CO_2R^{12}$ or $SO_2R^{15}$;

$R^9$ is selected from the group
- H, and
- lower alkyl;

$R^{10}$ is selected from the group
- lower alkyl,
- aryl, and
- aryl substituted by halogen or $NR^5R^6$;

$R^{11}$ is selected from the group
- H,
- lower alkyl, and
- lower alkyl substituted by oxo and halogen;

$R^{12}$ is selected from the group
- H,
- lower alkyl, and
- lower alkyl substituted by $NR^5R^6$ or $OR^{11}$;

$R^{13}$ and $R^{14}$ are each independently selected from the group
- H,
- lower alkyl,
- lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo,
- cycloalkyl,
- cycloalkyl substituted by $CO_2R^{12}$, $OR^{12}$, $NR^5R^6$, $CONR^5R^6$ or $SO_2R^{15}$,
- aryl,
- aryl substituted by $NR^5R^6$, $OR^{12}$, $CO_2R^{12}$, $CONR^5R^6$, $SO_2R^{15}$, halogen, lower alkyl, and lower alkyl substituted by halogen, $OR^{12}$, oxo, $CO_2R^{12}$, $C(O)NR^5R^6$ or $NR^5R^6$;
- $SO_2R^{15}$,
- $CO_2R^{12}$, and
- $COR^{12}$, or alternatively, the group —$NR^{13}R^{14}$ can form a ring having a total of from 3 to 7 ring atoms, said ring atoms comprising in addition to the nitrogen to which $R^{13}$ and $R^{14}$ are bonded, carbon ring atoms, said carbon ring atoms optionally being replaced by one or more additional N or O ring atoms, and said ring atoms optionally being substituted by OH, oxo, $NR^5R^6$, lower alkyl and lower alkyl substituted by $OR^{12}$;

$R^{15}$ is selected from the group
- aryl,
- aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
- heteroaryl,
- heteroaryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $NR^5R^6$ or $NR^5R^6$,
- $NR^5R^6$,
- lower alkyl,
- lower alkyl substituted by halogen, $OR^{12}$, oxo, $CO_2R^{12}$, $C(O)NR^5R^6$ or $NR^5R^6$,
- heterocycle, and
- heterocycle substituted by the group $CO_2R^{12}$, $COR^{12}$, $SO_2R^{12}$, lower alkyl, $C(O)NR^5R^6$ or $NR^5R^6$;

$R^{16}$ and $R^{17}$ are each independently selected from the group
- H, and
- lower alkyl, or, alternatively, the group —$NR^{16}R^{17}$ can form a ring having a total of from 3 to 7 ring atoms, said ring atoms comprising in addition to the nitrogen to which $R^{16}$ and $R^{17}$ are bonded, carbon ring atoms, said carbon ring atoms optionally being replaced by one or more additional N or O ring atoms, and said ring atoms optionally being substituted by lower alkyl, OH, oxo and $NH_2$; and n is 0, 1 or 2;

or the pharmaceutically acceptable salts thereof.

These compounds inhibit cyclin-dependent kinases, most particularly Cdk1, Cdk2 and Cdk4 These compounds and their pharmaceutically acceptable salts have antiproliferative activity and are useful in the treatment or control of cancer, in particular solid tumors.

The present invention also relates to pharmaceutical compositions comprising one or more compounds of the invention, or a pharmaceutically acceptable salt or ester thereof, and a pharmaceutically acceptable carrier or excipient.

The present invention further relates to a method for treating or controlling cancer, more particularly the treatment or control of a solid tumor, most particularly to the treatment or control of breast, lung and colon and prostate tumors by administering to a patient in need of such therapy a therapeutically effective amount of a compound of formula I, or a pharmaceutically salt or ester thereof.

DETAILED DESCRIPTION OF THE INVENTION

Definitions

As used herein, the following terms shall have the following definitions.

"Alkoxy" means any alkyl radical that is attached to the remainder of the molecule by oxygen and is often designated by the monovalent radical RO—. Examples include methoxy, ethoxy, etc.

"Aryl" means a monovalent, monocyclic or bicyclic, aromatic carbocyclic hydrocarbon radical, preferably a 6-10 membered aromatic aromatic ring system. Preferred aryl groups include, but are not limited to, phenyl, naphthyl, tolyl and xylyl.

"Carbonyl" means the radical C=O.

"Cycloalkyl" means a non-aromatic, partially or completely saturated monovalent cyclic hydrocarbon radical containing 3 to 8 atoms. Examples of cycloalkyl groups include cyclopropyl, cyclobutyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine, preferably fluorine or chlorine.

"Hetero atom" means an atom selected from N, O and S.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole, benzofuran and tetrazoly. Preferred ring systems include benzofuran, benzo oxazole and thiophene.

"Heterocycle" or "heterocyclyl" means a saturated or partially unsaturated, non-aromatic cyclic radical of 3 to 8 ring atoms in which from one to 3 ring atoms are hetero atoms selected from nitrogen, oxygen, S(O)n (where n is an integer from 0 to 2), or a combination thereof, the remaining ring atoms being C. Examples of preferred heterocycles are piperidine, piperazine, pyrrolidine, morpholine, indoline, tetrahydropyranyl, thiomorpholino, pentamethylene sulfide, and pentamethylene sulfone.

"$IC_{50}$" refers to the concentration of a particular compound according to the invention required to inhibit 50% of a specific measured activity. $IC_{50}$ can be measured, inter alia, as is described in Example 19A, infra.

"$K_i$" refers to a measure of the thermodynamic binding of the ligand/inhibitor (that is, a compound according to the invention) to the target protein. $K_i$ can be measured, inter alia, as is described in Example 19B, infra.

"Lower alkyl" alone or in conjunction with another term, e.g. lower alkyl-heterocycle, denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Oxo" means =O.

"Pharmaceutically acceptable ester" refers to a conventionally esterified compound of formula I having a carboxyl group, which esters retain the biological effectiveness and properties of the compounds of formula ₁ and are cleaved in vivo (in the organism) to the corresponding active carboxylic acid. Further information concerning examples of and the use of esters for the delivery of pharmaceutical compounds is available in Design of Prodrugs. Bundgaard H ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluene sulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flow ability and solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options, meaning that more than one substituent may be present simultaneously at various sites.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

In one embodiment, the present invention relates to compounds of formula I

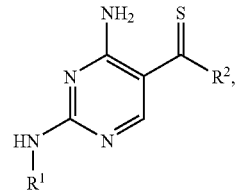

or the pharmaceutically acceptable salts thereof, wherein $R^1$ and $R^2$ are as defined above.

In a preferred embodiment of the compounds of formula I, $R^2$ is aryl, preferably phenyl, more preferably phenyl substituted by halogen, most preferably F, or $OR^{12}$ wherein $R^{12}$ is lower alkyl. In a most preferred embodiment, $R^2$ is phenyl substituted by one or two F molecules and one $OR^{12}$ group wherein $R^{12}$ is lower alkyl, preferably methyl.

In another preferred embodiment of the compounds of formula I, $R^2$ is heteroaryl, preferably benzofuran, benzo oxazole or benzoazole, most preferably benzofuran preferably substituted by halogen, most preferably F.

In another preferred embodiment of the compounds of formula I, $R^2$ is cycloalkyl, preferably cyclopentyl or cyclohexyl, each of which optionally may be substituted with lower alkyl and/or alkoxy.

In another preferred embodiment of the compounds of formula I, $R^2$ is heterocycle, preferably piperidine, pyrrolidine or pentamethylene sulfide, each of which optionally may be substituted with lower alkyl or alkoxy.

In another preferred embodiment of the compounds of formula I, $R^2$ is as defined above and $R^1$ is a heterocycle, preferably piperidine or pyrrolidine, and most preferably substituted by $S(O)_n R^{15}$ wherein n is 2 and $R^{15}$ is lower alkyl, $NH_2$ or heteroaryl. Also preferred are heterocycles substituted by the group $CO_2R^7$ wherein $R^7$ is lower alkyl.

In another preferred embodiment of the compounds of formula I, $R^2$ is as defined above and $R^1$ cycloalkyl, preferably cyclohexyl, and most preferably cyclohexane substituted by $NR^5R^6$ wherein $R^5$ and $R^6$ are H or one of $R^5$ or $R^6$ is $SO_2R^{15}$ and preferably $R^{15}$ is lower alkyl or lower alkyl substituted by $NR^5R^6$.

In another preferred embodiment of the compounds of formula I, $R^2$ is as defined above and $R^1$ is a lower alkyl-heterocycle.

In another preferred embodiment of the compounds of formula I, $R^2$ is as defined above and $R^1$ is aryl, preferably phenyl, and most preferably phenyl substituted by $S(O)_nR^{15}$ wherein $R^{15}$ is lower alkyl, preferably methyl.

In another preferred embodiment of the compounds of formula I, $R^2$ is as defined above and $R^1$ is a lower alkyl, preferably ethyl and propyl, and most preferably lower alkyl substituted by $NR^5R^6$ wherein one of $R^5$ or $R^6$ is $SO_2R^{15}$ and $R^{15}$ is lower alkyl. Examples of such compounds include:

N-{3-[4-Amino-5-(5-fluoro-2-methoxy-thiobenzoyl)-pyrimidin-2-ylamino]-propyl}-methanesulfonamide (Example 8).

In another preferred embodiment, $R^1$ selected from the group (a) 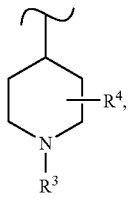

(b) 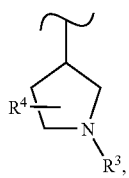

(c) 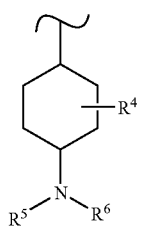

(d) 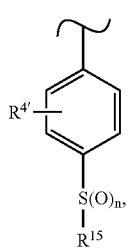

wherein
$R^3$ is selected from the group
H,
lower alkyl,
lower alkyl substituted by oxo, $OR^{12}$, $CO_2R^{12}$, $NR^5R^6$, $SO_2R^{15}$ or $C(O)NR^5R^6$,
$CO_2R^7$,
$COR^{12}$,
$C(O)NR^5R^6$, and
$SO_2R^{15}$;
$R^4$ is selected from the group
H,
$OR^{11}$,
lower alkyl,
$NR^5R^6$,
$NO_2$,
oxo
CN, and
halogen;
$R^{4'}$ is selected from the group
H,
$OR^{11}$,
lower alkyl,
$NR^5R^6$,
$NO_2$,
CN, and
halogen;

$R^5$ and $R^6$ are each independently selected from the group
H,
lower alkyl,
lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo,
cycloalkyl,
cycloalkyl substituted by $CO_2R^{12}$, $OR^{12}$, $NR^{13}R^{14}$, $C(O)NR^{13}R^{14}$ or $SO_2R^{15}$,
aryl,
aryl substituted by $NR^{13}R^{14}$, $OR^{12}$, $CO_2R^{12}$, $CONR^{13}R^{14}$, $SO_2R^{15}$, halogen, lower alkyl, and lower alkyl substituted by halogen, $OR^{12}$, oxo, $CO_2R^{12}$, $CONR^{13}R^{14}$ or $NR^{13}R^{14}$;
$SO_2R^{15}$,
$CO_2R^{12}$, and
$COR^{12}$,
or alternatively, the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $N^{13}R^{14}$, lower alkyl and lower alkyl substituted by $OR^{12}$;
$R^7$ is selected from the group
H,
lower alkyl,
lower alkyl substituted by $OR^{12}$, $CO_2R^{12}$, $NR^5R^6$, $CONR^5R^6$, halogen or oxo,
cycloalkyl,
cycloalkyl substituted by OH, oxo, or $NH_2$,
$SO_2R^{15}$, and
$COR^{12}$;
$R^{10}$ is selected from the group
lower alkyl,
aryl, and
aryl substituted by halogen or $NR^5R^6$;
$R^{11}$ is selected from the group
H,
lower alkyl, and
lower alkyl substituted by oxo and halogen;
$R^{12}$ is selected from the group
H
lower alkyl, and
lower alkyl substituted by halogen, oxo, $NR^5R^6$ or $OR^{11}$;
$R^{13}$ and $R^{14}$ are independently selected from
H,
lower alkyl,
lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo,
cycloalkyl,
cycloalkyl substituted by $CO_2R^{12}$, $OR^{12}$, $NR^5R^6$, $C(O)NR^5R^6$ or $SO_2R^{15}$,
aryl,
aryl substituted by $NR^5R^6$, $OR^{12}$, $CO_2R^{12}$, $C(O)NR^5R^6$, $SO_2R^{15}$, halogen, lower alkyl, and lower alkyl substituted by halogen, $OR^{12}$, oxo, $CO_2R^{12}$, $C(O)NR^5R^6$ and $NR^5R^6$;
$SO_2R^{15}$,
$CO_2R^{12}$, and
$COR^{12}$,
or alternatively, the group —$NR^{13}R^{14}$ can form a ring having a total of from 3 to 7 ring atoms, said ring atoms comprising in addition to the nitrogen to which $R^{13}$ and $R^{14}$ are bonded, carbon ring atoms, said carbon ring atoms optionally being replaced by one or more additional N or O ring atoms, and said ring atoms optionally being substituted by OH, oxo, $NR^5R^6$, $OR^{12}$, lower alkyl and lower alkyl substituted by $OR^{12}$;

$R^{15}$ is selected from the group
  aryl,
  aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
  heteroaryl,
  heteroaryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$, $NR^5R^6$,
  lower alkyl,
  lower alkyl substituted by the group halogen, $OR^{12}$, oxo, $CO_2R^{12}$, $C(O)NR^5R^6$ or $NR^5R^6$,
  heterocycle, and
  heterocycle substituted by the group $CO_2R^{12}$, $COR^{12}$, $SO_2R^{12}$, lower alkyl, $C(O)NR^5R^6$ or $NR^5R^6$; and
n is 0, 1 or 2, or the pharmaceutically acceptable salts thereof.

In another preferred embodiment, the invention relates to compounds of formula

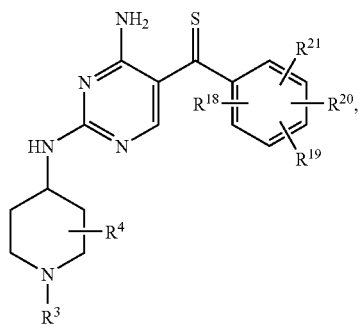

I(a)

wherein $R^3$ and $R^4$ are as defined above and $R^{18}$, $R^{19}$, $R^{20}$ and $R^{21}$ are each independently selected from lower alkyl, halogen and $OR^{12}$. Preferably, $R^3$ is selected from the group $CO_2R^7$, $COR^{12}$ and $SO_2R^{15}$. Most preferably $R^3$ is $SO_2R^{15}$ and $R^{15}$ is lower alkyl or $NR^5R^6$. Preferred $R^4$ groups include H, $OR^{11}$ and lower alkyl. Preferred $R^5$ and $R^6$ groups are those wherein the group $-NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms and said ring atoms optionally being substituted by OH, oxo, $NH_2$, lower alkyl or lower alkyl substituted by $OR^{12}$.

Examples of compounds of formula I(a) include:
[4-Amino-2-(1-methanesulfonyl-piperidin-4-ylamino)-pyrimidin-5-yl]-(2,3-difluoro-6-methoxy-phenyl)-methanethione (Example 1);
4-[4-Amino-5-(2,3-difluoro-6-methoxy-thiobenzoyl)-pyrimidin-2-ylamino]-piperidine-1-sulfonic acid amide (Example 4);
[4-Amino-2-(1-methanesulfonyl-piperidin-4-ylamino)-pyrimidin-5-yl]-(5-fluoro-2-methoxy-phenyl)-methanethione (Example 5);
[4-Amino-2-(1-methanesulfonyl-piperidin-4-ylamino)-pyrimidin-5-yl]-(5,6-difluoro-benzofuran-7-yl)-methanethione (Example 6);
[4-Amino-2-(1-methanesulfonyl-piperidin-4-ylamino)-pyrimidin-5-yl]-(5,6-difluoro-benzooxazol-7-yl)-methanethione (Example 7);
{4-Amino-2-[1-(3-morpholin-4-yl-propane-1-sulfonyl)-piperidin-4-ylamino]-pyrimidin-5-yl}(2,3-difluoro-6-methoxy-phenyl)-methanethione (Example 9);
{4-Amino-2-[1-(pyridine-2-sulfonyl)-piperidin-4-ylamino]-pyrimidin-5-yl}(2,3-difluoro-6-methoxy-phenyl)-methanethione (Example 10);
[4-Amino-2-(1-methanesulfonyl-piperidin-4-ylamino)-pyrimidin-5-yl]-thiophen-2-yl-methanethione (Example 11);
[4-Amino-2-(1-methanesulfonyl-piperidin-4-ylamino)-pyrimidin-5-yl]-(6-chloro-2,3-difluoro-phenyl)-methanethione (Example 13);
[4-Amino-2-(1-methanesulfonyl-piperidin-4-ylamino)-pyrimidin-5-yl]-(2,6-difluoro-phenyl)-methanethione (Example 15);
[4-Amino-2-(1-methanesulfonyl-piperidin-4-ylamino)-pyrimidin-5-yl]-phenyl-methanethione (Example 16);
4-[4-Amino-5-(5-fluoro-2-methoxy-thiobenzoyl)-pyrimidin-2-ylamino]-piperidine-1-carboxylic acid tert-butyl ester (Example 17); and
[4-Amino-2-(1-methanesulfonyl-pyrrolidin-3-ylamino)-pyrimidin-5-yl]-(2,3-difluoro-6-methoxy-phenyl)-methanethione (Example 18).

Another preferred embodiment of the invention relates to compounds of formula

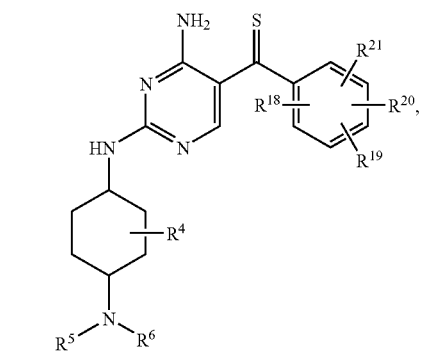

I(c)

wherein $R^4$, $R^5$, $R^6$, $R^{18}$, $R^{19}$, $R^{20}$ and $R^{21}$ are as defined above. Most preferably $R^4$ is H, one of $R^5$ or $R^6$ is H or lower alkyl and the other is $SO_2R^{15}$, wherein $R^{15}$ is lower alkyl, and two of $R^{18}$-$R^{21}$ are halogen, most preferably F, and one of $R^{18}$-$R^{21}$ is $COR^{12}$, wherein $R^{12}$ is lower alkyl, most preferably methyl.

Examples of such compounds include:
N-{4-[4-Amino-5-(2,3-difluoro-6-methoxy-thiobenzoyl)-pyrimidin-2-ylamino]-cyclohexyl}methanesulfonamide (Example 2);
N-{4-[4-Amino-5-(2,3-difluoro-6-methoxy-thiobenzoyl)-pyrimidin-2-ylamino]-cyclohexyl}-N-methylmethanesulfonamide (Example 3)

Another preferred embodiment of the invention relates to compounds of formula

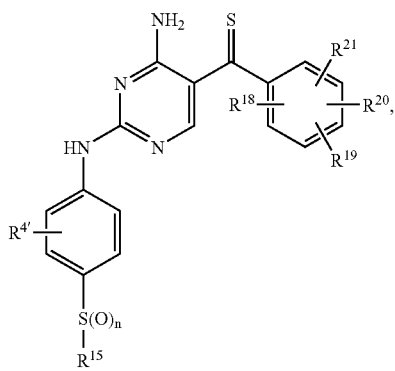

I(d)

wherein $R^{4'}$, $R^{15}$, $R^{18}$, $R^{19}$, $R^{20}$ and $R^{21}$ are as defined above. Most preferably n is 2, $R^{4'}$ is H, $R^{15}$ is lower alkyl, preferably methyl, or $R^{15}$ is $NR^5R^6$, wherein $R^5$ and $R^6$ are H, and two of $R^{18-21}$ are halogen, preferably F, and one of $R^{18-21}$ is $OR^{12}$, wherein $R^{12}$ is lower alkyl, preferably methyl. Examples of such compounds include:

[4-Amino-2-(4-methanesulfonyl-phenylamino)-pyrimidin-5-yl]-(2,3-difluoro-6-methoxy-phenyl)-methanethione (Example 12), and
4-[4-Amino-5-(2,3-difluoro-6-methoxy-thiobenzoyl)-pyrimidin-2-ylamino]-benzenesulfonamide (Example 14).

The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above.

General Synthesis of Compounds According to the Invention

The compounds of the present invention can be prepared by any conventional means. Suitable processes for synthesizing these compounds are provided in the examples. Generally, compounds of formula I can be prepared according to the following scheme using starting materials that can be prepared according to the procedures described in US 2004/0162303 A1, which, to the extent necessary, is herein incorporated by reference:

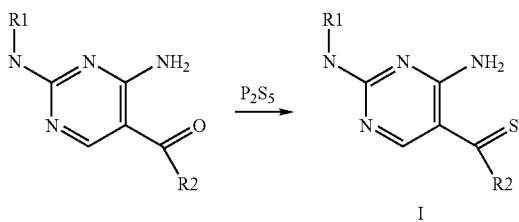

wherein $R^1$ and $R^2$ are as herein defined.

Separating a Mixture of Stereoisomers into the Optically Pure Stereoisomers (when Compound of Formula I is Chiral)

The optional separation of isomeric structures of formula I can be carried out according to known methods such as for example resolution or chiral high pressure liquid chromatography (also known as chiral HPLC). Resolution methods are well known, and are summarized in "Enantiomers, Racemates, and Resolutions" (Jacques, J. et al. John Wiley and Sons, New York, 1981). Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., New York 1983, pp. 87-124).

Converting a Compound of Formula I that Bears a Basic Nitrogen into a Pharmaceutically Acceptable Acid Addition Salt The optional conversion of a compound of formula I that bears a basic nitrogen into a pharmaceutically acceptable acid addition salt can be effected by conventional means. For example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluene sulfonic acid, or the like.

Compositions/Formulations

In an alternative embodiment, the present invention includes pharmaceutical compositions comprising at least one compound of formula I, or a pharmaceutically acceptable salt or ester thereof and an a pharmaceutically acceptable excipient and/or carrier.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention, including the compounds of formula I, are useful in the treatment or control of cell proliferative disorders, including chemoprevention of cancer. Chemoprevention is defined as inhibiting the development of invasive cancer by either blocking the initiating mutagenic event or by blocking the progression of pre-malignant cells that have already suffered an insult of inhibiting tumor relapse. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

Combinations

The compounds of this invention may be used in combination (administered in combination or sequentially) with known anti-cancer treatments such as radiation therapy or with cytostatic or cytotoxic agents, such as for example, but not limited to, DNA interactive agents, such as cisplatin or doxorubicin; topoisomerase II inhibitors such as etoposide: topoisomerase I inhibitors such as CPT-11 or topotecan; tublin interacting agents, such as paclitaxel, docetaxel or epothilones; hormonal agents such as tamoxifen: thymidilaate synthases inhibitors, such as 5-fluorouracil; and anti-metabolites such as methotrexate. Compounds of formula I may also be useful in combination with modulators of p53 transactivation.

If formulated as a fixed dose, the above-described combination products include the compounds of this invention within the dosage range described above and the other pharmaceutically active agent or treatment within its approved dose range. For example, an early cdk1 inhibitor olomucine has been found to act synergistically with well known cytotoxic agents in inducing apoptosis. (*J. Cell Sci.*, 1995, 108, 2897-2904). Compounds of formula I may also be administered sequentially with known anticancer or cytoxic agents when concomitant administration or a combination is inappropriate. This invention is not limited in the sequence of administration: compounds of formula I may be administered either prior to or after administration of the known anticancer or cytotoxic agent. For example, the cytotoxic activity of the cdk inhibitor flavopiridol is affected by the sequence of administration with anticancer agents. (*Cancer Research*, 1997, 57, 3375).

EXAMPLES

The following examples illustrate preferred methods for synthesizing and using the compounds and formulations of the present invention. These examples and preparations are illustrative and are not intended to be limiting. It should be understood that there may be other embodiments which fall within the spirit and scope of the invention as defined by the claims appended hereto.

Example 1

[4-Amino-2-(1-methanesulfonyl-piperidin-4-ylamino)-pyrimidin-5-yl]-(2,3-difluoro-6-methoxy-phenyl)-methanethione

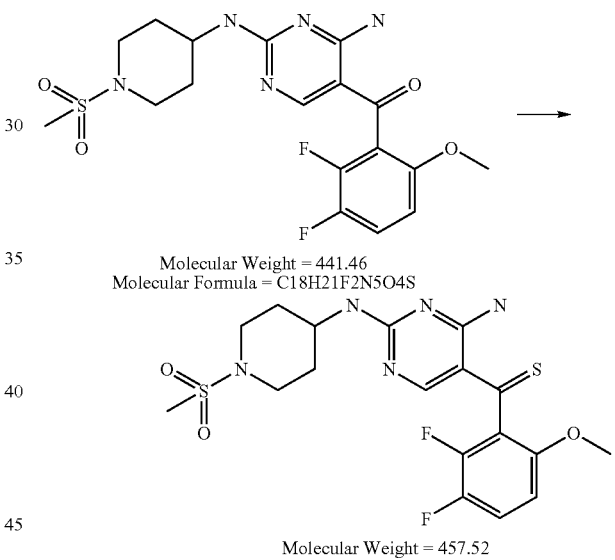

Molecular Weight = 441.46
Molecular Formula = C18H21F2N5O4S

Molecular Weight = 457.52
Molecular Formula = C18H21F2N5O3S2

To a solution of [4-Amino-2-(1-methanesulfonyl-piperidin-4-ylamino)-pyrimidin-5-yl]-(2,3-difluoro-6-methoxy-phenyl)-methanone (prepared in accordance with US 2004/0162303 A1, 810 mg, 1.84 mmol) in 1.4-dioxane at reflux were added phoporous pentasulfide (888 mg, 2 mmol, Aldrich). The mixture was stirred at reflux for 1.5 hours and then cooled to room temperature. Saturated sodium bicarbonate (20 ml) was added and the resulting mixture was stirred for 30 min. The mixture was extracted with ethyl acetate (3×20 mL) and the extracts were combined and dried ($Na_2SO_4$). The residue was then chromatographed on an ISCO machine with ethyl acetate and hexane as eluent (30% EtOAc/Hexanes from 0 to 4 min.; 40% from 4 to 9 min.; 50% from 9 to 12 min.; 60% from 12 to 15 min.; 70% from 15 to 20 min. and 100% from 20 min. to 30 min.) to give an orange solid after removal of solvent. 630 mg, 75%. LC/MS $(m+H)^+$: 458.

Example 2

N-{4-[4-Amino-5-(2,3-difluoro-6-methoxy-thiobenzoyl)-pyrimidin-2-ylamino]-cyclohexyl}methanesulfonamide

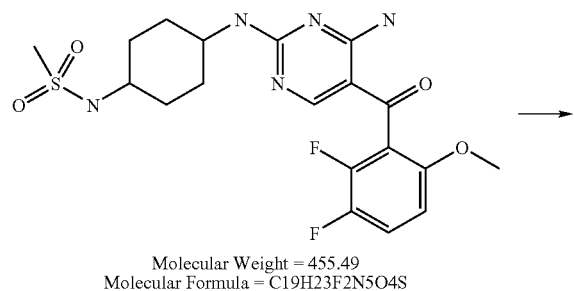

Molecular Weight = 455.49
Molecular Formula = C19H23F2N5O4S

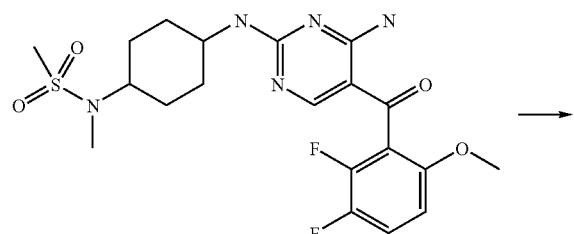

Molecular Weight = 471.55
Molecular Formula = C19H23F2N5O3S2

By a similar procedure to the preparation of the compound of Example 1, N-{4-[4-Amino-5-(2,3-difluoro-6-methoxy-thiobenzoyl)-pyrimidin-2-ylamino]-cyclohexyl}methanesulfonamide was made from N-{4-[4-Amino-5-(2,3-difluoro-6-methoxy-benzoyl)-pyrimidin-2-ylamino]-cyclohexyl}methanesulfonamide (prepared in accordance with US 2004/0162303 A1, 200 mg). LC/MS (m+H)+: 472.

Example 3

N-{4-[4-Amino-5-(2,3-difluoro-6-methoxy-thiobenzoyl)-pyrimidin-2-ylamino]-cyclohexyl}-N-methyl-methanesulfonamide

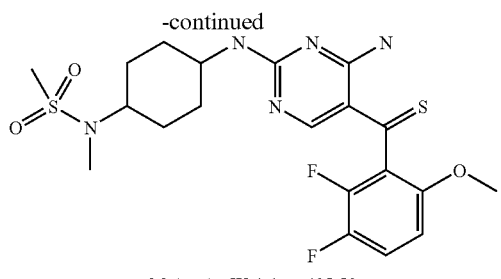

Molecular Weight = 469.51
Molecular Formula = C20H25F2N5O4S

-continued

Molecular Weight = 485.58
Molecular Formula = C20H25F2N5O3S2

By a similar procedure to the preparation of the compound of Example 1, N-{4-[4-Amino-5-(2,3-difluoro-6-methoxy-thiobenzoyl)-pyrimidin-2-ylamino]-cyclohexyl}-N-methyl-methanesulfonamide was made from N-{4-[4-Amino-5-(2,3-difluoro-6-methoxy-benzoyl)-pyrimidin-2-ylamino]-cyclohexyl}N-methyl-methanesulfonamide (prepared in accordance with US 2004/0162303 A1, 40 mg). LC/MS (m+H)+: 486.

Example 4

4-[4-Amino-5-(2,3-difluoro-6-methoxy-thiobenzoyl)-pyrimidin-2-ylamino]-piperidine-1-sulfonic acid amide

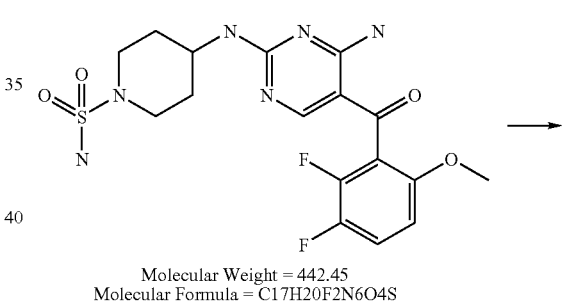

Molecular Weight = 442.45
Molecular Formula = C17H20F2N6O4S

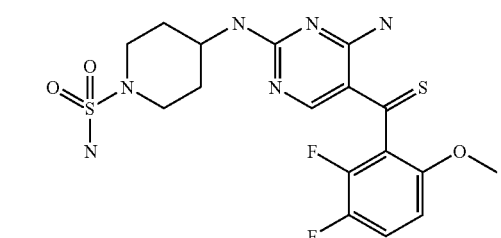

Molecular Weight = 458.51
Molecular Formula = C17H20F2N6O3S2

By a similar procedure to the preparation of the compound of Example 1, 4-[4-Amino-5-(2,3-difluoro-6-methoxy-thiobenzoyl)-pyrimidin-2-ylamino]-piperidine-1-sulfonic acid amide was made from 4-[4-Amino-5-(2,3-difluoro-6-methoxy-benzoyl)-pyrimidin-2-ylamino]-piperidine-1-sulfonic acid amide (prepared in accordance with US 2004/0162303 A1, 80 mg). LC/MS (m+H)+: 459.

Example 5

[4-Amino-2-(1-methanesulfonyl-piperidin-4-ylamino)-pyrimidin-5-yl]-(5-fluoro-2-methoxy-phenyl)-methanethione

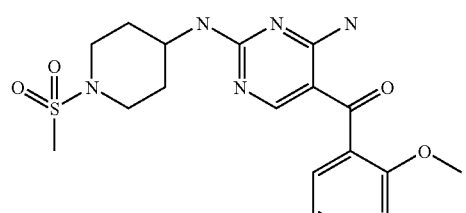

Molecular Weight = 423.47
Molecular Formula = C18H22FN5O4S

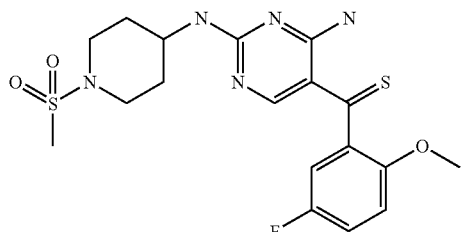

Molecular Weight = 439.53
Molecular Formula = C18H22FN5O3S2

By a similar procedure to the preparation of the compound of Example 1, [4-Amino-2-(1-methanesulfonyl-piperidin-4-ylamino)-pyrimidin-5-yl]-(5-fluoro-2-methoxy-phenyl)-methanethione was made from [4-Amino-2-(1-methanesulfonyl-piperidin-4-ylamino)-pyrimidin-5-yl]-(5-fluoro-2-methoxy-phenyl)-methanone (prepared in accordance with US 2004/0162303 A1, 40 mg). LC/MS (m+H)$^+$: 440.

Example 6

[4-Amino-2-(1-methanesulfonyl-piperidin-4-ylamino)-pyrimidin-5-yl]-(5,6-difluoro-benzofuran-7-yl)-methanethione

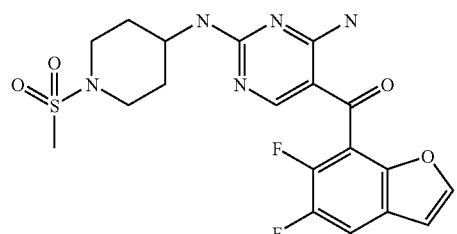

Molecular Weight = 451.46
Molecular Formula = C19H19F2N5O4S

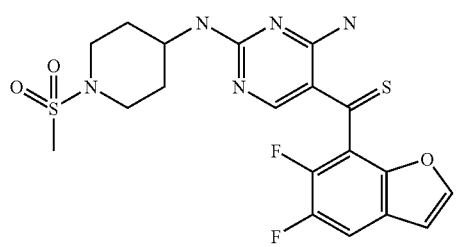

Molecular Weight = 467.52
Molecular Formula = C19H19F2N5O3S2

By a similar procedure to the preparation of the compound of Example 1, [4-Amino-2-(1-methanesulfonyl-piperidin-4-ylamino)-pyrimidin-5-yl]-(5,6-difluoro-benzofuran-7-yl)-methanethione was made from [4-Amino-2-(1-methanesulfonyl-piperidin-4-ylamino)-pyrimidin-5-yl]-(5,6-difluorobenzofuran-7-yl)-methanone (prepared in accordance with US 2004/0162303 A1, 130 mg). LC/MS (m+H)$^+$: 468.

Example 7

[4-Amino-2-(1-methanesulfonyl-piperidin-4-ylamino)-pyrimidin-5-yl]-(5,6-difluoro-benzooxazol-7-yl)-methanethione

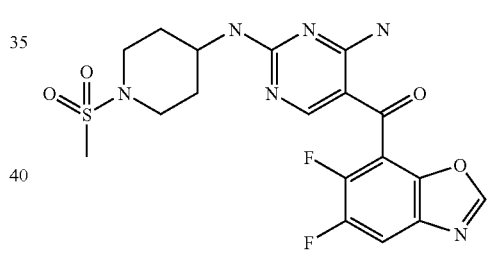

Molecular Weight = 452.44
Molecular Formula = C18H18F2N6O4S

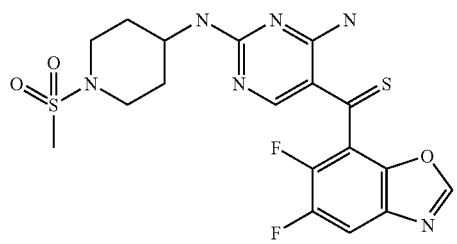

Molecular Weight = 468.51
Molecular Formula = C18H18F2N6O3S2

By a similar procedure to the preparation of the compound of Example 1, [4-Amino-2-(1-methanesulfonyl-piperidin-4-ylamino)-pyrimidin-5-yl]-(5,6-difluoro-benzooxazol-7-yl)-methanethione was made from [4-Amino-2-(1-methanesulfonyl-piperidin-4-ylamino)-pyrimidin-5-yl]-(5,6-difluoro-benzooxazol-7-yl)-methanone (prepared in accordance with US 2004/0162303 A1, 40 mg). LC/MS (m+H)$^+$: 469.

Example 8

N-{3-[4-Amino-5-(5-fluoro-2-methoxy-thiobenzoyl)-pyrimidin-2-ylamino]-propyl}-methanesulfonamide

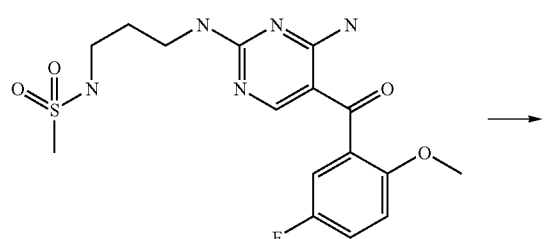

Molecular Weight = 397.43
Molecular Formula = C16H20FN5O4S

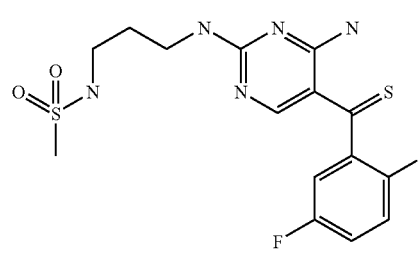

Molecular Weight = 413.50
Molecular Formula = C16H20FN5O3S2

By a similar procedure to the preparation of the compound of Example 1, N{3-[4-Amino-5-(5-fluoro-2-methoxy-thiobenzoyl)-pyrimidin-2-ylamino]-propyl}-methanesulfonamide was made from N-{3-[4-Amino-5-(5-fluoro-2-methoxy-benzoyl)-pyrimidin-2-ylamino]-propyl}-methanesulfonamide (prepared in accordance with US 2004/0162303 A1, 70 mg). LC/MS (m+H)$^+$: 414.

Example 9

{4-Amino-2-[1-(3-morpholin-4-yl-propane-1-sulfonyl)-piperidin-4-ylamino]-pyrimidin-5-yl}(2,3-difluoro-6-methoxy-phenyl)-methanethione

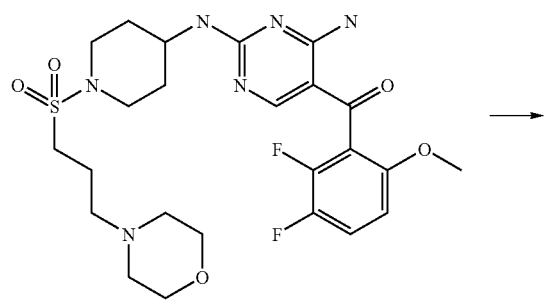

Molecular Weight = 553.63
Molecular Formula = C25H33F2N5O5S

-continued

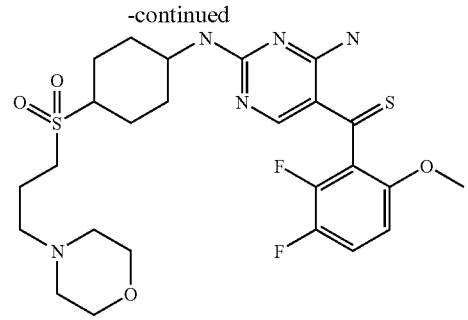

Molecular Weight = 569.70
Molecular Formula = C25H33F2N5O4S2

By a similar procedure to the preparation of the compound of Example 1, {4-Amino-2-[4-(3-morpholin-4-yl-propane-1-sulfonyl)-cyclohexylamino]-pyrimidin-5-yl}(2,3-difluoro-6-methoxy-phenyl)-methanethione was made from {4-Amino-2-[4-(3-morpholin-4-yl-propane-1-sulfonyl)-cyclohexylamino]-pyrimidin-5-yl}(2,3-difluoro-6-methoxy-phenyl)-methanone (prepared in accordance with US 2004/0162303 A1, 60 mg). LC/MS (m+H)$^+$: 570.

Example 10

{4-Amino-2-[1-(pyridine-2-sulfonyl)-piperidin-4-ylamino]-pyrimidin-5-yl}-(2,3-difluoro-6-methoxy-phenyl)-methanethione

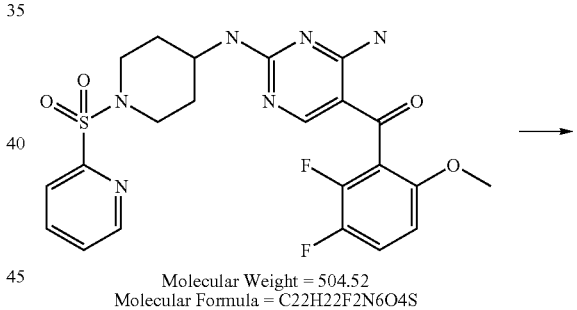

Molecular Weight = 504.52
Molecular Formula = C22H22F2N6O4S

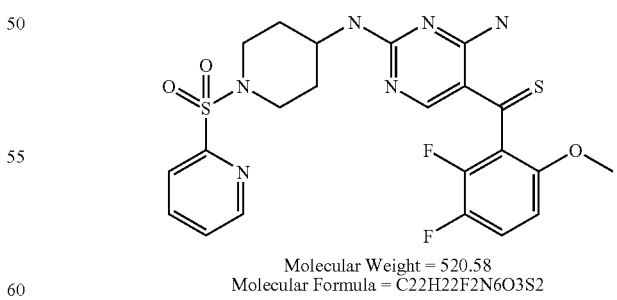

Molecular Weight = 520.58
Molecular Formula = C22H22F2N6O3S2

By a similar procedure to the preparation of the compound of Example 1, {4-Amino-2-[1-(pyridine-2-sulfonyl)-piperidin-4-ylamino]-pyrimidin-5-yl}-(2,3-difluoro-6-methoxy-phenyl)-methanethione was made from {4-Amino-2-[1-(pyridine-2-sulfonyl)-piperidin-4-ylamino]-pyrimidin-5-yl}-(2, 3-difluoro-6-methoxy-phenyl)-methanone (prepared in accordance with US 2004/0162303 A1, 50 mg). LC/MS (m+H)+: 521.

Example 11

[4-Amino-2-(1-methanesulfonyl-piperidin-4-ylamino)-pyrimidin-5-yl]-thiophen-2-yl-methanethione

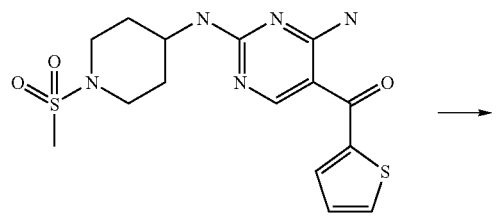

Molecular Weight = 381.48
Molecular Formula = C15H19N5O3S2

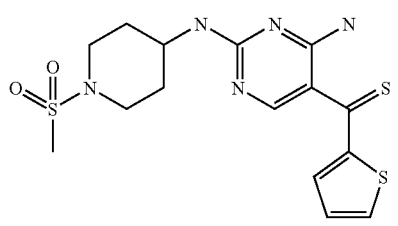

Molecular Weight = 397.54
Molecular Formula = C15H19N5O2S3

By a similar procedure to the preparation of the compound of Example 1, [4-Amino-2-(1-methanesulfonyl-piperidin-4-ylamino)-pyrimidin-5-yl]-thiophen-2-yl-methanethione was made from [4-Amino-2-(1-methanesulfonyl-piperidin-4-ylamino)-pyrimidin-5-yl]-thiophen-2-yl-methanone (prepared in accordance with US 2004/0162303 A1, 80 mg). LC/MS (m+H)+: 398.

Example 12

[4-Amino-2-(4-methanesulfonyl-phenylamino)-pyrimidin-5-yl]-(2,3-difluoro-6-methoxy-phenyl)-methanethione

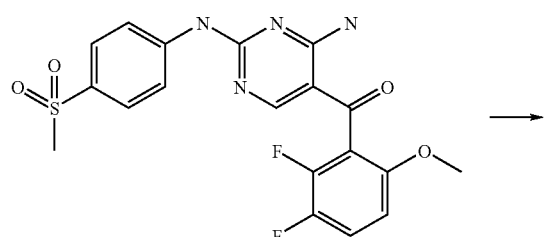

Molecular Weight = 434.42
Molecular Formula = C19H16F2N4O4S

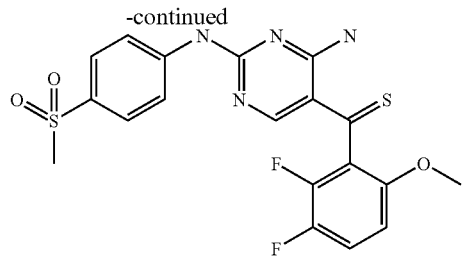

Molecular Weight = 450.49
Molecular Formula = C19H16F2N4O3S2

By a similar procedure to the preparation of Example 1, [4-Amino-2-(4-methanesulfonyl-phenylamino)-pyrimidin-5-yl]-(2,3-difluoro-6-methoxy-phenyl)-methanethione was made from [4-Amino-2-(4-methanesulfonyl-phenylamino)-pyrimidin-5-yl]-(2,3-difluoro-6-methoxy-phenyl)-methanone (prepared in accordance with US 2004/0162303 A1, 104 mg). LC/MS (m+H)+: 451.

Example 13

[4-Amino-2-(1-methanesulfonyl-piperidin-4-ylamino)-pyrimidin-5-yl]-(6-chloro-2,3-difluoro-phenyl)-methanethione

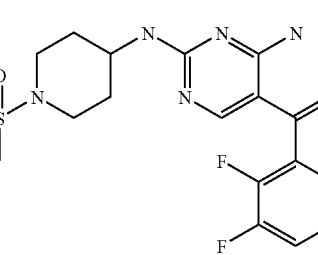

Molecular Weight = 445.88
Molecular Formula = C17H18ClF2N5O3S

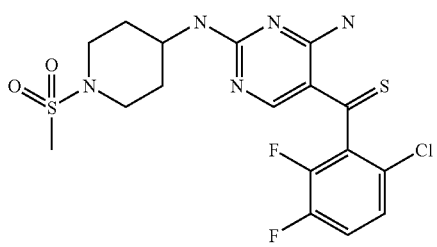

Molecular Weight = 461.94
Molecular Formula = C17H18ClF2N5O2S2

By a similar procedure to the preparation of the compound of Example 1, [4-Amino-2-(1-methanesulfonyl-piperidin-4-ylamino)-pyrimidin-5-yl]-(6-chloro-2,3-difluoro-phenyl)-methanethione was made from [4-Amino-2-(1-methanesulfonyl-piperidin-4-ylamino)-pyrimidin-5-yl]-(6-chloro-2,3-difluoro-phenyl)-methanone (prepared in accordance with US 2004/0162303 A1, 60 mg). LC/MS (m+H)+: 462.9.

Example 14

4-[4-Amino-5-(2,3-difluoro-6-methoxy-thiobenzoyl)-pyrimidin-2-ylamino]-benzenesulfonamide Molecular Weight = 435.41
Molecular Formula = C18H15F2N5O4S Molecular Weight = 451.48
Molecular Formula = C18H15F2N5O3S2

By a similar procedure to the preparation of the compound of Example 1, 4-[4-Amino-5-(2,3-difluoro-6-methoxy-thiobenzoyl)-pyrimidin-2-ylamino]-benzenesulfonamide was made from 4-[4-Amino-5-(2,3-difluoro-6-methoxy-benzoyl)-pyrimidin-2-ylamino]-benzenesulfonamide (prepared in accordance with US 2004/0162303 A1, 50 mg). LC/MS (m+H)$^+$: 452.

Example 15

[4-Amino-2-(1-methanesulfonyl-piperidin-4-ylamino)-pyrimidin-5-yl]-(2,6-difluoro-phenyl)-methanethione Molecular Weight = 411.43
Molecular Formula = C17H19F2N5O3S Molecular Weight = 427.50
Molecular Formula = C17H19F2N5O2S2

By a similar procedure to the preparation of the compound of Example 1, [4-Amino-2-(1-methanesulfonyl-piperidin-4-ylamino)-pyrimidin-5-yl]-(2,6-difluoro-phenyl)-methanethione was made from [4-Amino-2-(1-methanesulfonyl-piperidin-4-ylamino)-pyrimidin-5-yl]-(2,6-difluoro-phenyl)-methanone (prepared in accordance with US 2004/0162303 A1, 80 mg). LC/MS (m+H)$^+$: 428.

Example 16

[4-Amino-2-(1-methanesulfonyl-piperidin-4-ylamino)-pyrimidin-5-yl]-phenyl-methanethione Molecular Weight = 375.45
Molecular Formula = C17H21N5O3S Molecular Weight = 391.52
Molecular Formula = C17H21N5O2S2

By a similar procedure to the preparation of the compound of Example 1, [4-Amino-2-(1-methanesulfonyl-piperidin-4-ylamino)-pyrimidin-5-yl]-phenyl-methanethione was made from [4-Amino-2-(1-methanesulfonyl-piperidin-4-ylamino)-pyrimidin-5-yl]-phenyl-methanone (prepared in accordance with US 2004/0162303 A1, 56 mg). LC/MS (m+H)$^+$: 392.

Example 17

4-[4-Amino-5-(5-fluoro-2-methoxy-thiobenzoyl)-pyrimidin-2-ylamino]-piperidine-1-carboxylic acid tert-butyl ester

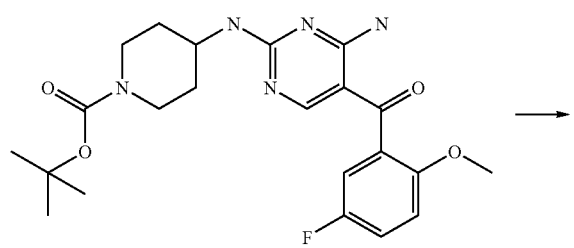

Molecular Weight = 445.50
Molecular Formula = C22H28FN5O4

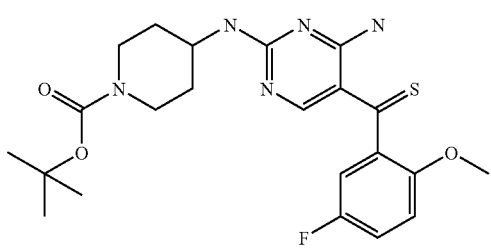

Molecular Weight = 461.56
Molecular Formula = C22H28FN5O3S

By a similar procedure to the preparation of the compound of Example 1, 4-[4-Amino-5-(5-fluoro-2-methoxy-thiobenzoyl)-pyrimidin-2-ylamino]-piperidine-1-carboxylic acid tert-butyl ester was made from 4-[4-Amino-5-(5-fluoro-2-methoxy-benzoyl)-pyrimidin-2-ylamino]-piperidine-1-carboxylic acid tert-butyl ester (prepared in accordance with US 2004/0162303 A1, 380 mg). LC/MS (m+H)$^+$: 462.

Example 18

[4-Amino-2-(1-methanesulfonyl-pyrrolidin-3-ylamino)-pyrimidin-5-yl]-(2,3-difluoro-6-methoxy-phenyl)-methanethione

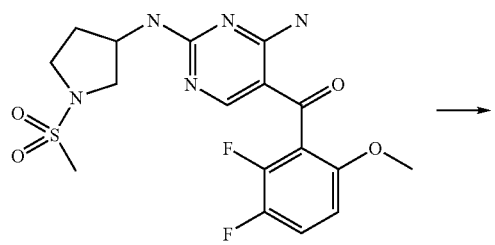

Molecular Weight = 427.43
Molecular Formula = C17H19F2N5O4S

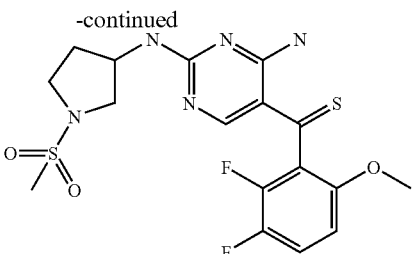

Molecular Weight = 443.50
Molecular Formula = C17H19F2N5O3S2

By a similar procedure to the preparation of the compound of Example 1, [4-Amino-2-(1-methanesulfonyl-pyrrolidin-3-ylamino)-pyrimidin-5-yl]-(2,3-difluoro-6-methoxy-phenyl)-methanethione was made from ([4-Amino-2-(1-methanesulfonyl-pyrrolidin-3-ylamino)-pyrimidin-5-yl]-(2,3-difluoro-6-methoxy-phenyl)-methanone (prepared in accordance with US 2004/0162303 A1, 60 mg). LC/MS (m+H)$^+$: 444.

The pharmacological properties of the compounds of this invention may be confirmed by a number of pharmacological assays. The exemplified pharmacological assays which follow have been carried out with the compounds according to the invention and their salts. The compounds of the invention exhibited Cdk1/cyclin A, Cdk2/cyclin E and/or Cdk4/cyclin D activity with Ki values of less than 0.5 µM. Additionally, the antiproliferative potency of some compounds of the invention was tested in the human colon tumor cell line HCT116 with IC$_{50}$ values reported from an MTT assay of less than 1.0 µM, preferably less than 0.5 µM, most preferably less than 0.2 µM.

The below-described kinase and cell based assays would be recognized by a medicinal chemist as reasonably correlating to prospective cancer therapy.

Example 19

Kinase Assays

A: IC$_{50}$ Measurement

To determine inhibition of Cdk4, Cdk2 and Cdk1 activity, kinase assays were conducted using FlashPlate™ assays (NEN™-Life Science Products). FlashPlate assays were performed using recombinant human cyclin B-CDK1, human cyclin E-CDK2 or human cyclin D1-CDK4 complexes. GST-cyclinE (GST-cycE), CDK2, GST-cyclinB (GST-cycB), CDK1, GST-CDK4 and cyclin D1 (cycD1) cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. *Cell* 1993, 75, 805-816). A 6×-Histidine tagged truncated form of retinoblastoma (Rb) protein (amino acid 386-928) was used as the substrate for the cycD1-CDK4, cycB-CDK1 and the cycE-CDK2 assays (the expression plasmid was provided by Dr. Veronica Sullivan, Department of Molecular Virology, Roche Research Centre, Welwyn Garden City, United Kingdom). The Rb protein is a natural substrate for phosphorylation by CDK4, CDK2 and CDK1 (see Herwig and Strauss *Eur. J. Biochem. Vol.* 246 (1997) pp. 581-601 and the references cited therein).

The expression of the 62 Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For all three kinase assays reported herein, 96-well Flash-Plates were coated with Rb protein at 10 µg/ml, using 100 µl per well. Plates were incubated at 4° C. overnight or at room temperature for 3 hours on a shaker. To control for nonspecific phosphorylation, one row of wells was coated with 100 µl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 µl reaction mix (25 mM HEPES, 20 mM $MgCl_2$, 0.002% Tween 20, 2 mM DTT, 1 µM ATP, 4 nM $^{33}$P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times 1 - \frac{\text{test compound} - \text{nonspecific}}{\text{total} - \text{nonspecific}}$$

where "test compound" refers to the average counts per minute of the test duplicates, "nonspecific" refers to the average counts per minute when no CyclinD/Cdk4, etc., was added, and "total" refers to the average counts per minute when no compound was added. The $IC_{50}$ value is the concentration of test compound that reduces by 50% the protein-kinase induced incorporation of the radiolabel under the test conditions described.

B: $K_i$ Measurement

Alternatively, inhibition activity may be measured using Ki. Using the protein constructs described above in Example 19A above, CDK1, CDK2, and CDK4 HTRF assays were set up. These were done in 96-well format and read in 384-well plate format. The assays were run at 3× their respective Kms for ATP.

In the CDK4 assay, test compounds were diluted to 3× their final concentrations in 25 mM Hepes, pH 7.0, 6.25 mM $MgCl_2$, 1.5 mM DTT, 135 µM ATP. The DMSO concentration was no greater than 4.76%. Twenty microliters were added to the wells of a 96-well plate. The kinase reaction was initiated by the addition of 40 µl/well of a solution containing 0.185 µM Rb and 2.25 µg/ml CDK4 in 25 mM Hepes, pH 7.0, 6.25 mM $MgCl_2$, 0.003% Tween-20, 0.3 mg/ml BSA, 1.5 mM DTT. Blank wells without CDK4 were included. The plates were incubated at 37° C. for 30 minutes with shaking. The kinase reaction was terminated by the addition of 15 µl/well of 1.6 uM anti-phospho-Rb (Ser 780) antibody (Cell Signaling Inc.) in 25 mM Hepes, pH 7.0, 24 mM EDTA, 0.2 mg/ml BSA. After 30 minutes at 37° C., 15 µl/well of 3 nM Lance-Eu-W1024 labeled anti-rabbit IgG and 60 nM Allophycocyanin conjugated anti-His6 (PerkinElmer Life Sciences) in 25 mM Hepes, pH 7.0, 0.5 mg/ml BSA were added. Following a one hour incubation at 37 deg C., 35 µl of each well, in duplicate, were transferred to 384-well black plates. The plates were read using either ViewLux or Victor V readers (PerkinElmer Life Sciences) using an excitation wavelength of 340 nm and dual emission wavelengths of 615 nm and 665 nm. IC50 values (the concentration of test compounds reducing the assay control fluorescence read-out by 50%) were first calculated from net readings at 665 nm, normalized for europium readings at 615 nm. For ATP competitive inhibitors, the Ki values were calculated according to the following equation:

$Ki=IC50/(1+S/Km)$ where S refers to the substrate concentration and Km refers to the Michaelis-Menten constant.

The CDK1 and CDK2 assays were similarly run except for small differences in reagent and protein concentrations:

The compound and enzyme buffers for both assays contained 10 mM $MgCl_2$. For CDK1 and CDK2, the respective reagent ATP concentrations were 162 uM and 90 uM. CDK1 at a reagent concentration of 0.15 ng/ul and CDK2 at a reagent concentration of 0.06 ng/ul were used. Reagent concentrations of detection reagents were adjusted between 3-12 nM Eu-Ab and 60-90 nM APC-antiHis 6 to give signal to background ratios of at least 10 to 1.

The results of this assay with respect to representative compounds of the invention are provided below in Table 1.

Example 20

Cell Based Assays (Tetrazolium Dye Proliferation Assay) ("MTT Assay")

Proliferation was evaluated by the tetrazolium dye assay according to the procedure of Denizot and Lang (Denizot, F. and Lang, R. *J Immunol Methods* 1986, 89, 271-277). The cell line used was HCT116, a colorectal carcinoma cell line obtained from the American Type Cell Culture Collection (ATCC; Rockville, Md.). The cells were grown in McCoy's 5A medium supplemented with 10% FCS and L-glutamine.

Cells were plated at the appropriate seeding density to give logarithmic growth over the course of the assay in a 96-well tissue culture plate. Plates were incubated overnight at 37° C. in a humidified incubator with 5% $CO_2$. The next day, test compounds were serially diluted to four times the final concentration in the appropriate medium containing 1.2% DMSO. One-fourth final volume of each dilution was added in duplicate to the plates containing cells. The same volume of 1.2% DMSO in medium was added to a row of "control wells" such that the final concentration of DMSO in each well was 0.3%. Wells to which no cells were added served as the "blank." Wells to which no inhibitor was added served as "no inhibitor control." The plates were) returned to the incubator, and at set time points (determined by their growth curves) plates were analyzed as described below.

3-(4,5-dimethylthiazole-2-yl)-2,5-diphenyl-2H-tetrazolium bromide (thiazolyl blue; MTT; Sigma) was added to each well to yield a final concentration of 1 mg/ml. Plates were returned to the incubator for 2.5-3 hours at 37° C. The MTT-containing medium was removed and the resulting formazan metabolite was solubilized in 100% ethanol with shaking for 15 minutes at room temperature. Absorbance readings were taken in a microtiter plate reader (Dynatech and Molecular Devices plate readers were used interchangeably) at a wavelength of 570 nm with a 650 nm reference. Percent inhibition (% INH) is calculated by subtracting the absorbance of the blank well from all wells, then subtracting the ratio of the average absorbance of each test duplicate ($S_{AVE}$) by the average of the controls ($C_{AVE}$) from 1.00. The final number is then multiplied by 100 (% INH=(1.00−$S_{AVE}$/$C_{AVE}$)×100). The concentration at which 50% inhibition of cell proliferation is obtained (the $IC_{50}$) is determined from the linear regression of a plot of the logarithm of the concentration versus percent inhibition.

The results of this assay with respect to representative compounds of the invention are provided below in Table 1.

TABLE 1

| Example | Name | Structure | Ki (uM) CDK1 | Ki (uM) CDK2 | Ki (uM) CDK4 | IC50 (uM) HCT116 |
|---|---|---|---|---|---|---|
| 1 | [4-Amino-2-(1-methanesulfonyl-piperidin-4-ylamino)-pyrimidin-5-yl]-(2,3-difluoro-6-methoxy-phenyl)-methanethione | | 0.00013 | 0.00012 | 0.00017 | 0.020 |
| 2 | N-{4-[4-Amino-5-(2,3-difluoro-6-methoxy-thiobenzoyl)-pyrimidin-2-ylamino]-cyclohexyl}-methanesulfonamide | | 0.00027 | 0.00018 | 0.00060 | 0.012 |
| 3 | N-{4-[4-Amino-5-(2,3-difluoro-6-methoxy-thiobenzoyl)-pyrimidin-2-ylamino]-cyclohexyl}-N-methyl-methanesulfonamide | | 0.00042 | 0.00027 | 0.00133 | 0.013 |
| 4 | 4-[4-Amino-5-(2,3-difluoro-6-methoxy-thiobenzoyl)-pyrimidin-2-ylamino]-piperidine-1-sulfonic acid amide | | <0.003 | <0.001 | <0.001 | 0.003 |
| 5 | [4-Amino-2-(1-methanesulfonyl-piperidin-4-ylamino)-pyrimidin-5-yl]-(5-fluoro-2-methoxy-phenyl)-methanethione | | <0.01 | 0.0013 | 0.0013 | 0.081 |

TABLE 1-continued

| Example | Name | Structure | Ki (uM) CDK1 | CDK2 | CDK4 | IC50 (uM) HCT116 |
|---|---|---|---|---|---|---|
| 6 | [4-Amino-2-(1-methanesulfonyl-piperidin-4-ylamino)-pyrimidin-5-yl]-(5,6-difluoro-benzofuran-7-yl)-methanethione | 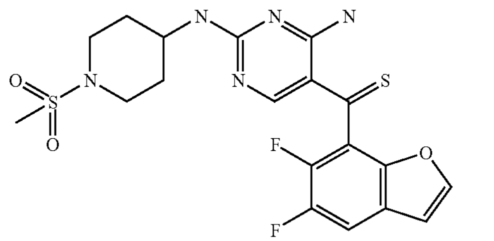 | 0.003 | 0.0001 | 0.00026 | 0.013 |
| 7 | [4-Amino-2-(1-methanesulfonyl-piperidin-4-ylamino)-pyrimidin-5-yl]-(5,6-difluoro-benzooxazol-7-yl)-methanethione | 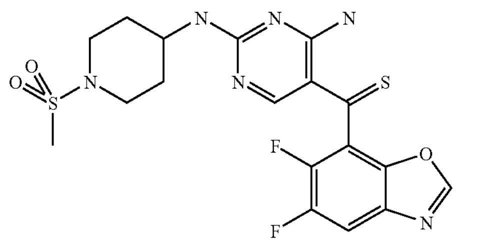 | 0.006 | 0.016 | 0.005 | NA |
| 8 | N-{3-[4-Amino-5-(5-fluoro-2-methoxy-thiobenzoyl)-pyrimidin-2-ylamino]-propyl}-methanesulfonamide | 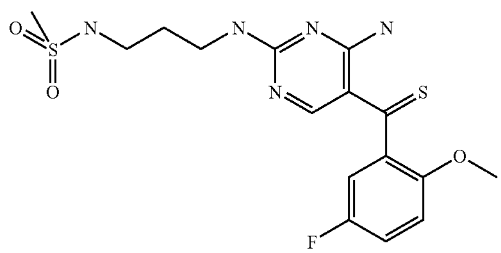 | 0.089 | 0.065 | 0.037 | NA |
| 9 | {4-Amino-2-[1-(3-morpholin-4-yl-propane-1-sulfonyl)-piperidin-4-yl-amino]-pyrimidin-5-yl}-(2,3-difluoro-6-methoxy-phenyl)-methanethione | 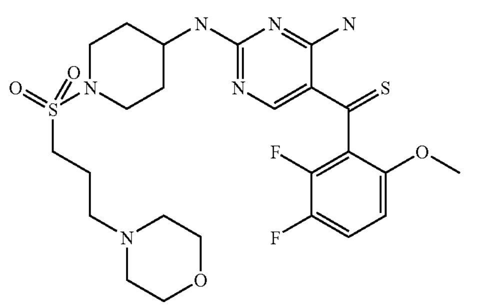 | 0.014 | 0.001 | 0.000 | NA |
| 10 | {4-Amino-2-[1-(pyridine-2-sulfonyl)-piperidin-4-ylamino]-pyrimidin-5-yl}-(2,3-difluoro-6-methoxy-phenyl)-methanethione | 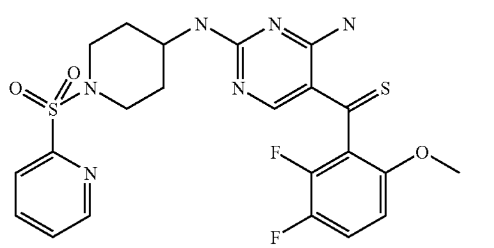 | 0.003 | 0.001 | 0.000 | NA |
| 11 | [4-Amino-2-(1-methanesulfonyl-piperidin-4-ylamino)-pyrimidin-5-yl]-thiophen-2-yl-methanethione | 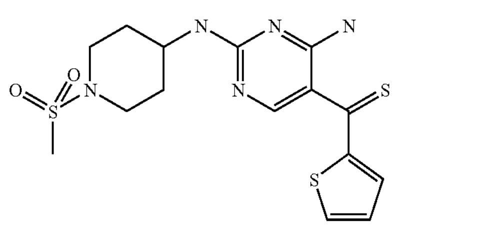 | 0.043 | 0.012 | 0.010 | NA |

TABLE 1-continued

| Example | Name | Structure | Ki (uM) CDK1 | Ki (uM) CDK2 | Ki (uM) CDK4 | IC50 (uM) HCT116 |
|---|---|---|---|---|---|---|
| 12 | [4-Amino-2-(4-methanesulfonyl-phenylamino)-pyrimidin-5-yl]-(2,3-difluoro-6-methoxy-phenyl)-methanethione | 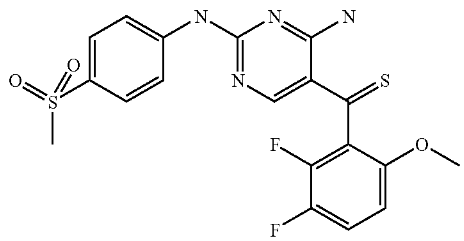 | 0.003 | 0.001 | 0.007 | NA |
| 13 | [4-Amino-2-(1-methanesulfonyl-piperidin-4-ylamino)-pyrimidin-5-yl]-(6-chloro-2,3-difluoro-phenyl)-methanethione | 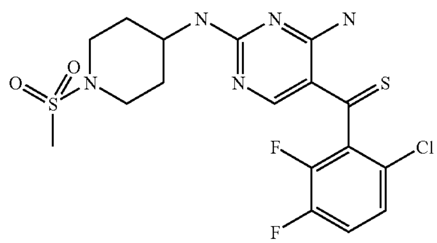 | 0.003 | 0.001 | 0.003 | 0.176 |
| 14 | 4-[4-Amino-5-(2,3-difluoro-6-methoxy-thiobenzoyl)-pyrimidin-2-ylamino]-benzenesulfonamide | 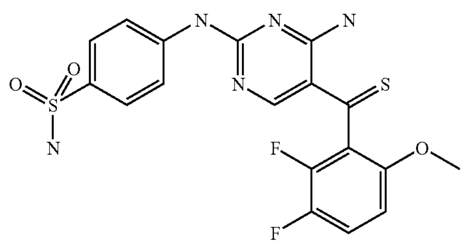 | 0.003 | 0.001 | 0.003 | 0.032 |
| 15 | [4-Amino-2-(1-methanesulfonyl-piperidin-4-ylamino)-pyrimidin-5-yl]-(2,6-difluoro-phenyl)methanethione | 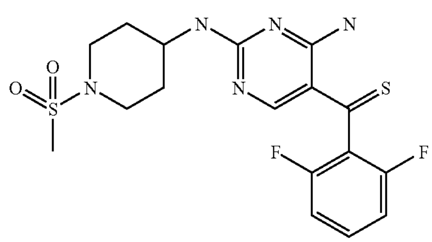 | 0.003 | 0.001 | 0.001 | 0.171 |
| 16 | [4-Amino-2-(1-methanesulfonyl-piperidin-4-ylamino)-pyrimidin-5-yl]-phenyl-methanethione | 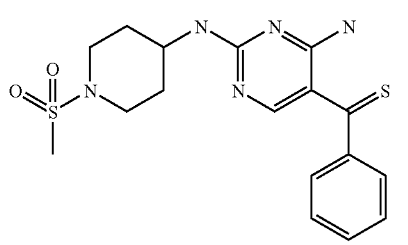 | 0.027 | 0.010 | 0.015 | NA |
| 17 | [4-Amino-2-(1-methanesulfonyl-piperidin-4-ylamino)-pyrimidin-5-yl]-(5-fluoro-2-methoxy-phenyl)-methanethione | 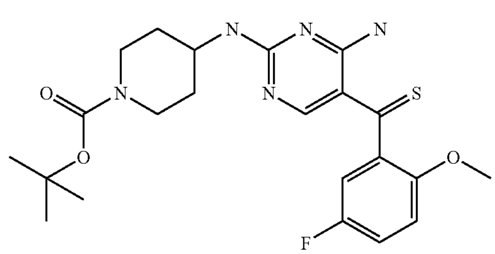 | 0.261 | 0.195 | NA | NA |

TABLE 1-continued

| | | | Ki (uM) | | | IC50 (uM) |
|---|---|---|---|---|---|---|
| Example | Name | Structure | CDK1 | CDK2 | CDK4 | HCT116 |
| 18 | [4-Amino-2-(1-methanesulfonyl-pyrrolidin-3-ylamino)-pyrimidin-5-yl]-(2,3-difluoro-6-methoxy-phenyl)-methanethione | | 0.000 | 0.001 | 0.0028 | NA |

Example 21

Tablet Formulation

| Item | Ingredients | Mg/Tablet | | | | | |
|---|---|---|---|---|---|---|---|
| 1 | Compound A * | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

* Compound A represents a compound of the invention.

Manufacturing Procedure:

1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 22

Capsule Formulation

| Item | Ingredients | mg/Capsule | | | | |
|---|---|---|---|---|---|---|
| 1 | Compound A * | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Compound A represents a compound of the invention.

Manufacturing Procedure:

1. Mix Items 1, 2 and 3 in a suitable mixer for 15 minutes.
2. Add Items 4 & 5 and mix for 3 minutes.
3. Fill into a suitable capsule.

Example 23

Injection Solution/Emulsion Preparation

| Item | Ingredient | mg/mL |
|---|---|---|
| 1 | Compound A * | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

Compound A represents a compound of the invention.

Manufacturing Procedure:

1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 μm filter and fill into vials.

Example 24

Injection Solution/Emulsion Preparation

| Item | Ingredient | mg/mL |
|---|---|---|
| 1 | Compound A * | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

Compound A represents a compound of the invention.

Manufacturing Procedure:

1. Dissolve item 1 in item 2.
2. Add items 3, 4 and 5 to item 6 and mix until dispersed, then homogenize.

3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be through routine experimentation and practice of the invention. Thus, the invention is intended not to be limited by the foregoing description, but to be defined by the appended claims and their equivalents.

The invention claimed is:
1. A compound of the formula

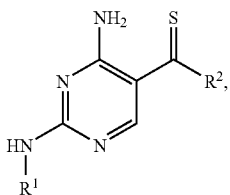

wherein
R$^1$ is selected from the group
heterocycle and lower alkyl-heterocycle, wherein the heterocycle moiety in both instances optionally may be substituted by up to four substituents independently selected from
H,
lower alkyl,
lower alkyl substituted by oxo, OR$^{12}$, CO$_2$R$^{12}$, NR5R6, S(O)$_n$R$^{15}$ or C(O)NR$^5$R$^6$,
CO$_2$R$^7$,
COR$^{11}$,
COR$^{12}$,
C(O)NR$^{13}$R$^{14}$,
S(O)$_n$R$^{15}$,
oxo,
OR$^{12}$; or
NR$^5$R$^6$,
aryl,
aryl substituted by
H,
S(O)$_n$—R$^{15}$,
NR$^5$R$^6$,
carbonyl,
carbonyl substituted by lower alkyl, OR$^{12}$ or NR$^5$R$^6$,
lower alkyl,
lower alkyl substituted by OR$^{10}$ or NR$^5$R$^6$,
OR$^8$;
halogen,
cycloalkyl,
cycloalkyl substituted by OR$^7$, NR$^5$R$^6$ or S(O)$_n$R$^{15}$,
lower alkyl, and
lower alkyl substituted by
NR$^5$R$^6$,
NR$^{11}$SO$_2$R$^{15}$,
CO$_2$R$^{10}$,
S(O)$_n$R$^{15}$,
heterocycle,
heterocycle substituted by
lower alkyl,
CO$_2$R$^{12}$ or
SO$_2$R$^{15}$,
heteroaryl,
heteroaryl substituted by
lower alkyl,
CO$_2$R$^{12}$, or
SO$_2$R$^{15}$,
aryl, and
aryl substituted by
lower alkyl,
halogen,
NR$^5$R$^6$,
COR$^{12}$, or
CO$_2$R$^{12}$;
R$^2$ is selected from the group
aryl, heteroaryl, cycloalkyl and heterocycle, wherein each may be substituted by up to four substituents independently selected from the group
lower alkyl,
lower alkyl substituted by halogen or OR$^{10}$,
halogen,
OR$^{12}$,
NO$_2$,
CN,
NR$^5$R$^6$,
S(O)$_n$—R$^9$, and
SO$_2$—NR$^{16}$R$^{17}$;
R$^5$ and R$^6$ are each independently selected from the group
H,
lower alkyl,
lower alkyl substituted by oxo, CO$_2$R$^{12}$, OR$^{12}$, NR$^{13}$R$^{14}$, C(O)NR$^{13}$R$^{14}$, SO$_2$R$^{15}$, NSO$_2$R$^{12}$, heteroaryl, heterocycle, or heterocycle substituted by oxo,
cycloalkyl,
cycloalkyl substituted by CO$_2$R$^{12}$, OR$^{12}$, NR$^{13}$R$^{14}$, C(O)NR$^{13}$R$^{14}$ or SO$_2$R$^{15}$,
aryl,
aryl substituted by NR$^{13}$R$^{14}$, OR$^{12}$, CO$_2$R$^{12}$, C(O)NR$^{13}$R$^{14}$, SO$_2$R$^{15}$, halogen, lower alkyl, or lower alkyl substituted by halogen, OR$^{12}$, oxo, CO$_2$R$^{12}$, C(O)NR$^{13}$R$^{14}$ or NR$^{13}$R$^{14}$,
SO$_2$R$^{15}$,
CO$_2$R$^{12}$, and
COR$^{12}$,
or alternatively, the group —NR$^5$R$^6$ can form a ring having a total of from 3 to 7 ring atoms, said ring atoms comprising in addition to the nitrogen to which R$^5$ and R$^6$ are bonded, carbon ring atoms, said carbon ring atoms optionally being replaced by one or more additional N or O ring atoms or the group SO$_2$, and said ring atoms optionally being substituted by OH, oxo, NR$^{13}$R$^{14}$, lower alkyl and lower alkyl substituted by OR$^{12}$;
R$^7$ is selected from the group
H,
lower alkyl,
lower alkyl substituted by OR$^{12}$, CO$_2$R$^{12}$, NR$^5$R$^6$, C(O)NR$^5$R$^6$, halogen, oxo, aryl or aryl substituted by up to three substituents independently selected from lower alkyl, halogen and NR$^5$R$^6$,
cycloalkyl,
cycloalkyl substituted by OH, oxo, or NH$_2$,
SO$_2$R$^{15}$, and
COR$^{12}$;
R$^8$ is selected from the group
H,
lower alkyl,
lower alkyl substituted by NR$^5$R$^6$, heterocycle, and
heterocycle substituted by lower alkyl, $CO_2R^{12}$ or $SO_2R^{15}$;

$R^9$ is selected from the group
H, and
lower alkyl;

$R^{10}$ is selected from the group
lower alkyl,
aryl, and
aryl substituted by halogen or $NR^5R^6$;

$R^{11}$ is selected from the group
H,
lower alkyl, and
lower alkyl substituted by oxo and halogen;

$R^{12}$ is selected from the group
H,
lower alkyl, and
lower alkyl substituted by $NR^5R^6$ or $OR^{11}$;

$R^{13}$ and $R^{14}$ are each independently selected from the group
H,
lower alkyl,
lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo,
cycloalkyl,
cycloalkyl substituted by $CO_2R^{12}$, $OR^{12}$, $NR^5R^6$, $CONR^5R^6$ or $SO_2R^{15}$,
aryl,
aryl substituted by $NR^5R^6$, $OR^{12}$, $CO_2R^{12}$, $CONR^5R^6$, $SO_2R^{15}$, halogen, lower alkyl, and lower alkyl substituted by halogen, $OR^{12}$, oxo, $CO_2R^{12}$, $C(O)NR^5R^6$ or $NR^5R^6$;
$SO_2R^{15}$,
$CO_2R^{12}$, and
$COR^{12}$,
or alternatively, the group —$NR^{13}R^{14}$ can form a ring having a total of from 3 to 7 ring atoms, said ring atoms comprising in addition to the nitrogen to which $R^{13}$ and $R^{14}$ are bonded, carbon ring atoms, said carbon ring atoms optionally being replaced by one or more additional N or O ring atoms, and said ring atoms optionally being substituted by OH, oxo, $NR^5R^6$, lower alkyl and lower alkyl substituted by $OR^{12}$;

$R^{15}$ is selected from the group
aryl,
aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
heteroaryl,
heteroaryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $NR^5R^6$ or $NR^5R^6$,
$NR^5R^6$,
lower alkyl,
lower alkyl substituted by halogen, $OR^{12}$, oxo, $CO_2R^{12}$, $C(O)NR^5R^6$ or $NR^5R^6$,
heterocycle, and
heterocycle substituted by the group $CO_2R^{12}$, $COR^{12}$, $SO_2R^{12}$, lower alkyl, $C(O)NR^5R^6$ or $NR^5R^6$;

$R^{16}$ and $R^{17}$ are each independently selected from the group
H, and
lower alkyl, or, alternatively, the group —$NR^{16}R^{17}$ can form a ring having a total of from 3 to 7 ring atoms, said ring atoms comprising in addition to the nitrogen to which $R^{16}$ and $R^{17}$ are bonded, carbon ring atoms, said carbon ring atoms optionally being replaced by one or more additional N or O ring atoms, and said ring atoms optionally being substituted by lower alkyl, OH, oxo and $NH_2$; and n is 0, 1 or 2;

or the pharmaceutically acceptable salts thereof.

2. The compound of claim 1 wherein $R^2$ is phenyl substituted by two F molecules and one $OR^{12}$ and wherein $R^{12}$ is methyl.

3. The compound of claim 1 wherein $R^2$ is heteroaryl selected from benzofuran, benzooxazole and benzoazole.

4. The compound of claim 1 wherein $R^2$ is cyclohexyl that optionally is substituted by alkoxy.

5. The compound of claim 1 wherein $R^1$ is ethyl or propyl that optionally is substituted by $NR^5R^6$ wherein one of $R^5$ or $R^6$ is $SO_2R^{15}$ and $R^{15}$ is lower alkyl.

6. The compound of claim 5 which is N-{3-[4-Amino-5-(5-fluoro-2-methoxy-thiobenzoyl)-pyrimidin-2-ylamino]-propyl}-methanesulfonamide.

7. The compound of claim 1 wherein $R^1$ selected from the group

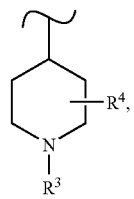

(a)

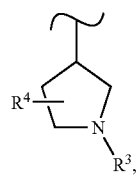

(b)

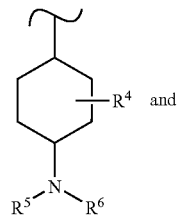

(c) and

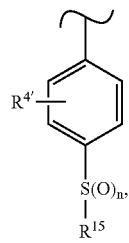

(d)

wherein $R^3$ is selected from the group
- H,
- lower alkyl,
- lower alkyl substituted by oxo, $OR^{12}$, $CO_2R^{12}$, $NR^5R^6$, $SO_2R^{15}$ or $C(O)NR^5R^6$,
- $CO_2R^7$,
- $COR^{12}$,
- $C(O)NR^5R^6$, and
- $SO_2R^{15}$;

$R^4$ is selected from the group
- H,
- $OR^{11}$,
- lower alkyl,
- $NR^5R^6$,
- $NO_2$,
- oxo
- CN, and
- halogen;

$R^{4'}$ is selected from the group
- H,
- $OR^{11}$,
- lower alkyl,
- $NR^5R^6$,
- $NO_2$,
- CN, and
- halogen;

$R^5$ and $R^6$ are each independently selected from the group
- H,
- lower alkyl,
- lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo,
- cycloalkyl,
- cycloalkyl substituted by $CO_2R^{12}$, $OR^{12}$, $NR^{13}R^{14}$, $C(O)NR^{13}R^{14}$ or $SO_2R^{15}$,
- aryl,
- aryl substituted by $NR^{13}R^{14}$, $OR^{12}$, $CO_2R^{12}$, $CONR^{13}R^{14}$, $SO_2R^{15}$, halogen, lower alkyl, and lower alkyl substituted by halogen, $OR^{12}$, oxo, $CO_2R^{12}$, $CONR^{13}R^{14}$ or $NR^{13}R^{14}$;
- $SO_2R^{15}$,
- $CO_2R^{12}$, and
- $COR^{12}$,
- or alternatively, the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $N^{13}R^{14}$, lower alkyl and lower alkyl substituted by $OR^{12}$;

$R^7$ is selected from the group
- H,
- lower alkyl,
- lower alkyl substituted by $OR^{12}$, $CO_2R^{12}$, $NR^5R^6$, or $CONR^5R^6$, halogen, oxo, aryl, aryl substituted by up to three substituents independently selected from lower alkyl, halogen, or $NR^5R^6$,
- cycloalkyl,
- cycloalkyl substituted by OH, oxo, or $NH_2$,
- $SO_2R^{15}$, and
- $COR^{12}$;

$R^{10}$ is selected from the group
- lower alkyl,
- aryl, and
- aryl substituted by halogen or $NR^5R^6$;

$R^{11}$ is selected from the group
- H,
- lower alkyl, and
- lower alkyl substituted by oxo and halogen;

$R^{12}$ is selected from the group
- H
- lower alkyl, and
- lower alkyl substituted by halogen, oxo, $NR^5R^6$ or $OR^{11}$;

$R^{13}$ and $R^{14}$ are independently selected from
- H,
- lower alkyl,
- lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo,
- cycloalkyl,
- cycloalkyl substituted by $CO_2R^{12}$, $OR^{12}$, $NR^5R^6$, $C(O)NR^5R^6$ or $SO_2R^{15}$,
- aryl,
- aryl substituted by $NR^5R^6$, $OR^{12}$, $CO_2R^{12}$, $C(O)NR^5R^6$, $SO_2R^{15}$, halogen, lower alkyl, and lower alkyl substituted by halogen, $OR^{12}$, oxo, $CO_2R^{12}$, $C(O)NR^5R^6$ and $NR^5R^6$;
- $SO_2R^{15}$,
- $CO_2R^{12}$, and
- $COR^{12}$,
- or alternatively, the group —$NR^{13}R^{14}$ can form a ring having a total of from 3 to 7 ring atoms, said ring atoms comprising in addition to the nitrogen to which $R^{13}$ and $R^{14}$ are bonded, carbon ring atoms, said carbon ring atoms optionally being replaced by one or more additional N or O ring atoms, and said ring atoms optionally being substituted by OH, oxo, $NR^5R^6$, lower alkyl and lower alkyl substituted by $OR^{12}$;

$R^{15}$ is selected from the group
- aryl,
- aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
- heteroaryl,
- heteroaryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
- $NR^5R^6$,
- lower alkyl,
- lower alkyl substituted by the group halogen, $OR^{12}$, oxo, $CO_2R^{12}$, $C(O)NR^5R^6$ or $NR^5R^6$,
- heterocycle, and
- heterocycle substituted by the group $CO_2R^{12}$, $COR^{12}$, $SO_2R^{12}$, lower alkyl, $C(O)NR^5R^6$ or $NR^5R^6$; and n is 0, 1 or 2, or the pharmaceutically acceptable salts thereof.

8. A compound of formula

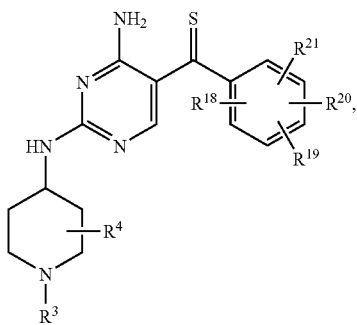

I(a)

wherein
R$^3$ is selected from the group
H,
lower alkyl,
lower alkyl substituted by oxo, OR$^{12}$, CO$_2$R$^{12}$, NR$^5$R$^6$, SO$_2$R$^{15}$ or C(O)NR$^5$R$^6$,
CO$_2$R$^7$,
COR$^{12}$,
C(O)NR$^5$R$^6$, and
SO$_2$R$^{15}$;
R$^4$ is selected from the group
H,
OR$^{11}$,
lower alkyl,
NR$^5$R$^6$,
NO$_2$,
oxo
CN, and
halogen;
R$^5$ and R$^6$ are each independently selected from the group
H,
lower alkyl,
lower alkyl substituted by oxo, CO$_2$R$^{12}$, OR$^{12}$, NR$^{13}$R$^{14}$, C(O)NR$^{13}$R$^{14}$, SO$_2$R$^{15}$, NSO$_2$R$^{12}$, heteroaryl, heterocycle, or heterocycle substituted by oxo,
cycloalkyl,
cycloalkyl substituted by CO$_2$R$^{12}$, OR$^{12}$, NR$^{13}$R$^{14}$, C(O)NR$^{13}$R$^{14}$ or SO$_2$R$^{15}$,
aryl,
aryl substituted by NR$^{13}$R$^{14}$, OR$^{12}$, CO$_2$R$^{12}$, CONR$^{13}$R$^{14}$, SO$_2$R$^{15}$, halogen, lower alkyl, and lower alkyl substituted by halogen, OR$^{12}$, oxo, CO$_2$R$^{12}$, CONR$^{13}$R$^{14}$ or NR$^{13}$R$^{14}$;
SO$_2$R$^{15}$,
CO$_2$R$^{12}$, and
COR$^{12}$,
or alternatively, the group —NR$^5$R$^6$ can form a ring having a total of from 3 to 7 ring atoms, said ring atoms comprising in addition to the nitrogen to which R$^5$ and R$^6$ are bonded, carbon ring atoms, said carbon ring atoms optionally being replaced by one or more additional N or O ring atoms or the group SO$_2$, and said ring atoms optionally being substituted by OH, oxo, N$^{13}$R$^{14}$, lower alkyl and lower alkyl substituted by OR$^{12}$;

R$^7$ is selected from the group
H,
lower alkyl,
lower alkyl substituted by OR$^{12}$, CO$_2$R$^{12}$, NR$^5$R$^6$, or CONR$^5$R$^6$, halogen, oxo, aryl, aryl substituted by up to three substituents independently selected from lower alkyl, halogen, or NR$^5$R$^6$,
cycloalkyl,
cycloalkyl substituted by OH, oxo, or NH$_2$,
SO$_2$R$^{15}$, and
COR$^{12}$;
R$^{11}$ is selected from the group
H,
lower alkyl, and
lower alkyl substituted by oxo and halogen;
R$^{12}$ is selected from the group
H
lower alkyl, and
lower alkyl substituted by halogen, oxo, NR$^5$R$^6$ or OR$^{11}$;
R$^{13}$ and R$^{14}$ are independently selected from
H,
lower alkyl,
lower alkyl substituted by CO$_2$R$^{12}$, OR$^{12}$, NR$^5$R$^6$, C(O)NR$^5$R$^6$, SO$_2$R$^{15}$, NSO$_2$R$^{12}$, heteroaryl, heterocycle, or heterocycle substituted by oxo,
cycloalkyl,
cycloalkyl substituted by CO$_2$R$^{12}$, OR$^{12}$, NR$^5$R$^6$, C(O)NR$^5$R$^6$ or SO$_2$R$^{15}$,
aryl,
aryl substituted by NR$^5$R$^5$, OR$^{12}$, CO$_2$R$^{12}$, C(O)NR$^5$R$^6$, SO$_2$R$^{15}$, halogen, lower alkyl, and lower alkyl substituted by halogen, OR$^{12}$, oxo, CO$_2$R$^{12}$, C(O)NR$^5$R$^6$ and NR$^5$R$^6$;
SO$_2$R$^{15}$,
CO$_2$R$^{12}$, and
COR$^{12}$,
or alternatively, the group —NR$^{13}$R$^{14}$ can form a ring having a total of from 3 to 7 ring atoms, said ring atoms comprising in addition to the nitrogen to which R$^{13}$ and R$^{14}$ are bonded, carbon ring atoms, said carbon ring atoms optionally being replaced by one or more additional N or O ring atoms, and said ring atoms optionally being substituted by OH, oxo, NR$^5$R$^6$, lower alkyl and lower alkyl substituted by OR$^{12}$;
R$^{15}$ is selected from the group
aryl,
aryl substituted by the group halogen, CO$_2$R$^{12}$, SO$_2$R$^{10}$, COR$^{12}$, lower alkyl and lower alkyl substituted by halogen, OR$^{12}$, oxo, CO$_2$R$^{12}$, C(O)NR$^5$R$^6$ or NR$^5$R$^6$,
heteroaryl,
heteroaryl substituted by the group halogen, CO$_2$R$^{12}$, SO$_2$R$^{10}$, COR$^{12}$, lower alkyl and lower alkyl substituted by halogen, OR$^{12}$, oxo, CO$_2$R$^{12}$, C(O)NR$^5$R$^6$ or NR$^5$R$^6$,
NR$^5$R$^6$,
lower alkyl,
lower alkyl substituted by the group halogen, OR$^{12}$, oxo, CO$_2$R$^{12}$, C(O)NR$^5$R$^6$ or NR$^5$R$^6$,
heterocycle, and
heterocycle substituted by the group CO$_2$R$^{12}$, COR$^{12}$, SO$_2$R$^{12}$, lower alkyl, C(O)NR$^5$R$^6$ or NR$^5$R$^6$;

$R^{18}$, $R^{19}$, $R^{20}$ and $R^{21}$ are each independently selected from
lower alkyl,
halogen, and
$OR^{12}$;
or the pharmaceutically acceptable salts thereof.

9. The compound of claim 8 wherein $R^3$ is selected from the group $CO_2R^7$, $COR^{12}$ and $SO_2R^{15}$ and $R^4$ is H, $OR^{11}$ or lower alkyl.

10. The compound of claim 8 that is selected from the group:
[4-Amino-2-(1-methanesulfonyl-piperidin-4-ylamino)-pyrimidin-5-yl]-(2,3-difluoro-6-methoxy-phenyl)-methanethione;
4-[4-Amino-5-(2,3-difluoro-6-methoxy-thiobenzoyl)-pyrimidin-2-ylamino]-piperidine-1-sulfonic acid amide;
[4-Amino-2-(1-methanesulfonyl-piperidin-4-ylamino)-pyrimidin-5-yl]-(5-fluoro-2-methoxy-phenyl)-methanethione;
[4-Amino-2-(1-methanesulfonyl-piperidin-4-ylamino)-pyrimidin-5-yl]-(5,6-difluoro-benzofuran-7-yl)-methanethione;
[4-Amino-2-(1-methanesulfonyl-piperidin-4-ylamino)-pyrimidin-5-yl]-(5,6-difluoro-benzooxazol-7-yl)-methanethione;
{4-Amino-2-[1-(3-morpholin-4-yl-propane-1-sulfonyl)-piperidin-4-ylamino]-pyrimidin-5-yl}(2,3-difluoro-6-methoxy-phenyl)-methanethione;
{4-Amino-2-[1-(pyridine-2-sulfonyl)-piperidin-4-ylamino]-pyrimidin-5-yl}-(2,3-difluoro-6-methoxy-phenyl)-methanethione;
[4-Amino-2-(1-methanesulfonyl-piperidin-4-ylamino)-pyrimidin-5-yl]-thiophen-2-yl-methanethione; and
[4-Amino-2-(1-methanesulfonyl-piperidin-4-ylamino)-pyrimidin-5-yl]-(6-chloro-2,3-difluoro-phenyl)-methanethione.

11. The compound of claim 8 that is selected from the group:
[4-Amino-2-(1-methanesulfonyl-piperidin-4-ylamino)-pyrimidin-5-yl]-(2,6-difluoro-phenyl)-methanethione;
[4-Amino-2-(1-methanesulfonyl-piperidin-4-ylamino)-pyrimidin-5-yl]-phenyl-methanethione;
4-[4-Amino-5-(5-fluoro-2-methoxy-thiobenzoyl)-pyrimidin-2-ylamino]-piperidine-1-carboxylic acid tert-butyl ester; and
[4-Amino-2-(1-methanesulfonyl-pyrrolidin-3-ylamino)-pyrimidin-5-yl]-(2,3-difluoro-6-methoxy-phenyl)-methanethione.

12. A compound of formula

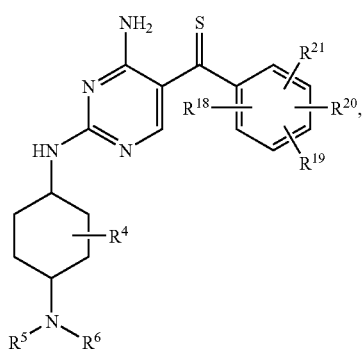

I(c)

wherein
$R^4$ is selected from the group
H,
$OR^{11}$,
lower alkyl,
$NR^5R^6$,
$NO_2$,
oxo
CN, and
halogen;
$R^5$ and $R^6$ are each independently selected from the group
H,
lower alkyl,
lower alkyl substituted by oxo, $CO_2R^{12}$, $OR^{12}$, $NR^{13}R^{14}$, $C(O)NR^{13}R^{14}$, $SO_2R^{15}$, $NSO_2R^{12}$, heteroaryl, heterocycle, or heterocycle substituted by oxo,
cycloalkyl,
cycloalkyl substituted by $CO_2R^{12}$, $OR^{12}$, $NR^{13}R^{14}$, $C(O)NR^{13}R^{14}$ or $SO_2R^{15}$,
aryl,
aryl substituted by $NR^{13}R^{14}$, $OR^{12}$, $CO_2R^{12}$, $CONR^{13}R^{14}$, $SO_2R^{15}$, halogen, lower alkyl, and lower alkyl substituted by halogen, $OR^{12}$, oxo, $CO_2R^{12}$, $CONR^{13}R^{14}$ or $NR^{13}R^{14}$;
$SO_2R^{15}$,
$CO_2R^{12}$, and
$COR^{12}$,
or alternatively, the group —$NR^5R^6$ can form a ring having a total of from 3 to 7 ring atoms, said ring atoms comprising in addition to the nitrogen to which $R^5$ and $R^6$ are bonded, carbon ring atoms, said carbon ring atoms optionally being replaced by one or more additional N or O ring atoms or the group $SO_2$, and said ring atoms optionally being substituted by OH, oxo, $N^{13}R^{14}$, lower alkyl and lower alkyl substituted by $OR^{12}$;
$R^{10}$ is selected from the group
lower alkyl,
aryl, and
aryl substituted by halogen or $NR^5R^6$;
$R^{11}$ is selected from the group
H,
lower alkyl, and
lower alkyl substituted by oxo and halogen;
$R^{12}$ is selected from the group
H
lower alkyl, and
lower alkyl substituted by halogen, oxo, $NR^5R^6$ or $OR^{11}$;
$R^{13}$ and $R^{14}$ are independently selected from
H,
lower alkyl,
lower alkyl substituted by $CO_2R^{12}$, $OR^{12}$, $NR^5R^6$, $C(O)NR^5R^6$, $SO_2R^{15}$, $NSO_2R^{12}$, heteroaryl, heterocycle, or heterocycle substituted by oxo,
cycloalkyl,
cycloalkyl substituted by $CO_2R^{12}$, $OR^{12}$, $NR^5R^6$, $C(O)NR^5R^6$ or $SO_2R^{15}$,
aryl,
aryl substituted by $NR^5R^6$, $OR^{12}$, $CO_2R^{12}$, $C(O)NR^5R^6$, $SO_2R^{15}$, halogen, lower alkyl, and lower alkyl substituted by halogen, $OR^{12}$, oxo, $CO_2R^{12}$, $C(O)NR^5R^6$ and $NR^5R^6$;
$SO_2R^{15}$,
$CO_2R^{12}$, and
$COR^{12}$, or alternatively, the group —NR$^{13}$R$^{14}$ can form a ring having a total of from 3 to 7 ring atoms, said ring atoms comprising in addition to the nitrogen to which R$^{13}$ and R$^{14}$ are bonded, carbon ring atoms, said carbon ring atoms optionally being replaced by one or more additional N or O ring atoms, and said ring atoms optionally being substituted by OH, oxo, NR$^5$R$^6$, lower alkyl and lower alkyl substituted by OR$^{12}$;

R$^{15}$ is selected from the group
aryl,
aryl substituted by the group halogen, CO$_2$R$^{12}$, SO$_2$R$^{10}$, COR$^{12}$, lower alkyl and lower alkyl substituted by halogen, OR$^{12}$, oxo, CO$_2$R$^{12}$, C(O)NR$^5$R$^6$ or NR$^5$R$^6$,
heteroaryl,
heteroaryl substituted by the group halogen, CO$_2$R$^{12}$, SO$_2$R$^{10}$, COR$^{12}$, lower alkyl and lower alkyl substituted by halogen, OR$^{12}$, oxo, CO$_2$R$^{12}$, C(O)NR$^5$R$^6$ or NR$^5$R$^6$,
NR$^5$R$^6$,
lower alkyl,
lower alkyl substituted by the group halogen, OR$^{12}$, oxo, CO$_2$R$^{12}$, C(O)NR$^5$R$^6$ or NR$^5$R$^6$,
heterocycle, and
heterocycle substituted by the group CO$_2$R$^{12}$, COR$^{12}$, SO$_2$R$^{12}$, lower alkyl, C(O)NR$^5$R$^6$ or NR$^5$R$^6$; and R$^{18}$, R$^{19}$, R$^{20}$ and R$^{21}$ are each independently selected from
lower alkyl,
halogen, and
OR$^{12}$;

or the pharmaceutically acceptable salts thereof.

13. The compound of claim 12 wherein R$^4$ is H, one of R$^5$ or R$^6$ is H or lower alkyl and the other is SO$_2$R$^{15}$, wherein R$^{15}$ is lower alkyl, and two of R$^{18}$-R$^{21}$ are halogen, and one of R$^{18}$-R$^{21}$ is COR$^{12}$, wherein R$^{12}$ is lower alkyl.

14. The compound of claim 12 which is selected from the group:
N-{4-[4-Amino-5-(2,3-difluoro-6-methoxy-thiobenzoyl)-pyrimidin-2-ylamino]-cyclohexyl}methanesulfonamide; and
N-{4-[4-Amino-5-(2,3-difluoro-6-methoxy-thiobenzoyl)-pyrimidin-2-ylamino]-cyclohexyl}-N-methylmethane-sulfonamide.

15. A compound of formula

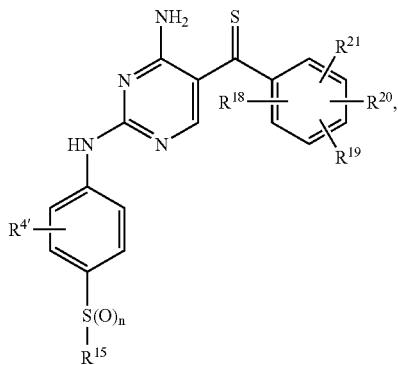

I(d)

wherein
R$^{4'}$ is selected from the group
H,
OR$^{11}$,
lower alkyl,
NR$^5$R$^6$,
NO$_2$,
CN, and
halogen;

R$^5$ and R$^6$ are each independently selected from the group
H,
lower alkyl,
lower alkyl substituted by oxo, CO$_2$R$^{12}$, OR$^{12}$, NR$^{13}$R$^{14}$, C(O)NR$^{13}$R$^{14}$, SO$_2$R$^{15}$, NSO$_2$R$^{12}$, heteroaryl, heterocycle, or heterocycle substituted by oxo,
cycloalkyl,
cycloalkyl substituted by CO$_2$R$^{12}$, OR$^{12}$, NR$^{13}$R$^{14}$, C(O)NR$^{13}$R$^{14}$ or SO$_2$R$^{15}$,
aryl,
aryl substituted by NR$^{13}$R$^{14}$, OR$^{12}$, CO$_2$R$^{12}$, CONR$^{13}$R$^{14}$, SO$_2$R$^{15}$, halogen, lower alkyl, and lower alkyl substituted by halogen, OR$^{12}$, oxo, CO$_2$R$^{12}$, CONR$^{13}$R$^{14}$ or NR$^{13}$R$^{14}$;
SO$_2$R$^{15}$,
CO$_2$R$^{12}$, and
COR$^{12}$,
or alternatively, the group —NR$^5$R$^6$ can form a ring having a total of from 3 to 7 ring atoms, said ring atoms comprising in addition to the nitrogen to which R$^5$ and R$^6$ are bonded, carbon ring atoms, said carbon ring atoms optionally being replaced by one or more additional N or O ring atoms or the group SO$_2$, and said ring atoms optionally being substituted by OH, oxo, N$^{13}$R$^{14}$, lower alkyl and lower alkyl substituted by OR$^{12}$;

R$^{11}$ is selected from the group
H,
lower alkyl, and
lower alkyl substituted by oxo and halogen;

R$^{12}$ is selected from the group
H
lower alkyl, and
lower alkyl substituted by halogen, oxo, NR$^5$R$^6$ or OR$^{11}$;

R$^{13}$ and R$^{14}$ are independently selected from
H,
lower alkyl,
lower alkyl substituted by CO$_2$R$^{12}$, OR$^{12}$, NR$^5$R$^6$, C(O)NR$^5$R$^6$, SO$_2$R$^{15}$, NSO$_2$R$^{12}$, heteroaryl, heterocycle, or heterocycle substituted by oxo,
cycloalkyl,
cycloalkyl substituted by CO$_2$R$^{12}$, OR$^{12}$, NR$^5$R$^6$, C(O)NR$^5$R$^6$ or
SO$_2$R$^{15}$,
aryl,
aryl substituted by NR$^5$R$^6$, OR$^{12}$, CO$_2$R$^{12}$, C(O)NR$^5$R$^6$, SO$_2$R$^{15}$, halogen, lower alkyl, and lower alkyl substituted by halogen, OR$^{12}$, oxo, CO$_2$R$^{12}$, C(O)NR$^5$R$^6$ and NR$^5$R$^6$;
SO$_2$R$^{15}$,
CO$_2$R$^{12}$, and
COR$^{12}$,
or alternatively, the group —NR$^{13}$R$^{14}$ can form a ring having a total of from 3 to 7 ring atoms, said ring atoms comprising in addition to the nitrogen to which R$^{13}$ and R$^{14}$ are bonded, carbon ring atoms, said carbon ring atoms optionally being replaced by one or more additional N or O ring atoms, and said ring atoms optionally being substituted by OH, oxo, $NR^5R^6$, lower alkyl and lower alkyl substituted by $OR^{12}$;

$R^{15}$ is selected from the group
aryl,
aryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
heteroaryl,
heteroaryl substituted by the group halogen, $CO_2R^{12}$, $SO_2R^{10}$, $COR^{12}$, lower alkyl and lower alkyl substituted by halogen, $OR^{12}$, oxo, $CO_2R^{12}$, $C(O)NR^5R^6$ or $NR^5R^6$,
$NR^5R^6$,
lower alkyl,
lower alkyl substituted by the group halogen, $OR^{12}$, oxo, $CO_2R^{12}$, $C(O)NR^5R^6$ or $NR^5R^6$,
heterocycle, and
heterocycle substituted by the group $CO_2R^{12}$, $COR^{12}$, $SO_2R^{12}$, lower alkyl, $C(O)NR^5R^6$ or $NR^5R^6$;

$R^{18}$, $R^{19}$, $R^{20}$ and $R^{21}$ are each independently selected from
lower alkyl,
halogen, and
$OR^{12}$; and
n is 0, 1 or 2,
or the pharmaceutically acceptable salts thereof.

16. The compound of claim 15 wherein n is 2, $R^{4'}$ is H and $R^{15}$ is lower alkyl or $NR^5R^6$.

17. The compound of claim 16 wherein $R^{15}$ is $NR^5R^6$ and wherein $R^5$ and $R^6$ are H.

18. The compound of claim 16 wherein two of $R^{18-21}$ are halogen and one of $R^{18-21}$ is $OR^{12}$, wherein $R^{12}$ is lower alkyl.

19. The compound of claim 15 which is selected from:
[4-Amino-2-(4-methanesulfonyl-phenylamino)-pyrimidin-5-yl]-(2,3-difluoro-6-methoxy-phenyl)-methanethione, and
4-[4-Amino-5-(2,3-difluoro-6-methoxy-thiobenzoyl)-pyrimidin-2-ylamino]-benzenesulfonamide.

20. A composition comprising as an active ingredient a therapeutically effective amount of a compound of claim 1 and a pharmaceutically acceptable carrier or excipient.

* * * * *